United States Patent
Formica

(10) Patent No.: US 11,623,059 B2
(45) Date of Patent: Apr. 11, 2023

(54) PIVOTABLE OUTLET PORT

(71) Applicant: ResMed Pty Ltd, Bella Vista (AU)

(72) Inventor: Justin John Formica, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 378 days.

(21) Appl. No.: 16/987,473

(22) Filed: Aug. 7, 2020

(65) Prior Publication Data

US 2021/0046273 A1 Feb. 18, 2021

Related U.S. Application Data

(60) Provisional application No. 62/885,557, filed on Aug. 12, 2019.

(51) Int. Cl.
| | | |
|---|---|---|
| A61M 16/08 | (2006.01) | |
| A61M 16/16 | (2006.01) | |
| A61M 16/06 | (2006.01) | |
| A61M 39/12 | (2006.01) | |
| F16L 27/107 | (2006.01) | |
| A61M 16/00 | (2006.01) | |
| A61M 39/10 | (2006.01) | |

(52) U.S. Cl.
CPC .... *A61M 16/0816* (2013.01); *A61M 16/0066* (2013.01); *A61M 16/0638* (2014.02); *A61M 16/0672* (2014.02); *A61M 16/0875* (2013.01); *A61M 16/16* (2013.01); *A61M 39/12* (2013.01); *F16L 27/107* (2013.01); *A61M 39/1055* (2013.01); *A61M 2202/0208* (2013.01); *A61M 2205/02* (2013.01); *A61M 2205/0216* (2013.01)

(58) Field of Classification Search
CPC .......... A61M 16/0057; A61M 16/0066; A61M 16/0069; A61M 16/08; A61M 16/0816; A61M 16/0825; A61M 16/0833; A61M 16/0875; A61M 16/16; A61M 39/12; F16L 27/107; F16L 27/108; F16L 27/11; A62B 18/006; A62B 18/045
See application file for complete search history.

(56) References Cited

U.S. PATENT DOCUMENTS

| | | | | |
|---|---|---|---|---|
| 4,401,241 A | * | 8/1983 | Cruz | A61M 11/042 222/527 |
| 4,461,425 A | * | 7/1984 | Miller | A61M 16/16 239/338 |
| 4,782,832 A | | 11/1988 | Trimble et al. | |

(Continued)

FOREIGN PATENT DOCUMENTS

| | | |
|---|---|---|
| WO | WO 98/004310 A1 | 2/1998 |
| WO | WO 98/034665 A1 | 8/1998 |

(Continued)

OTHER PUBLICATIONS

"*Respiratory Physiology*", by John B, West, Lippincott Williams & Wilkins, 9th edition published 2012 (8 pages).

Primary Examiner — Joseph D. Boecker
(74) Attorney, Agent, or Firm — Nixon & Vanderhye P.C.

(57) ABSTRACT

An apparatus for providing a pressurised flow of breathable gas to the airways of a patient includes a pivotable outlet port structured and arranged to connect to an air delivery tube configured to pass the pressurised flow of breathable gas to a patient interface. The pivotable outlet port is able to pivot about at least one axis.

20 Claims, 20 Drawing Sheets

(56) References Cited

U.S. PATENT DOCUMENTS

| | | | |
|---|---|---|---|
| 4,944,310 | A | 7/1990 | Sullivan |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2010/0065051 | A1* | 3/2010 | Potharaju .............. A61M 16/10 128/203.26 |
| 2015/0136127 | A1* | 5/2015 | Dimatteo .............. A61M 16/16 439/13 |
| 2018/0236200 | A1* | 8/2018 | Goldspink ........ A61M 16/0816 |
| 2021/0093825 | A1* | 4/2021 | Lin .................. A61M 16/0816 |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | WO 2014/138804 A1 | 9/2014 |
| WO | WO 2015/089582 A1 | 6/2015 |
| WO | WO-2018094452 A1 * | 5/2018 ........ A61M 16/0816 |

* cited by examiner

PIVOTABLE OUTLET PORT

1 CROSS-REFERENCE TO RELATED APPLICATIONS

This application claims the benefit of U.S. Provisional Application No. 62/885,557, filed Aug. 12, 2019, which is incorporated herein by reference in its entirety.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

| Table of noise output levels of prior RPT devices (one specimen only, measured using test method specified in ISO 3744 in CPAP mode at 10 cmH$_2$O). | | |
|---|---|---|
| RPT Device name | A-weighted sound pressure level dB(A) | Year (approx.) |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

Still another aspect of the present technology relates to an apparatus for humidifying a flow of breathable gas including a water reservoir including a cavity structured to hold a volume of water, a water reservoir dock structured and arranged to receive the water reservoir in an operative position, and an air delivery tube configured to pass the flow of breathable gas that has been humidified in the water reservoir to a patient interface.

Another aspect of the present technology relates to an apparatus for providing a pressurised flow of breathable gas to the airways of a patient including a pivotable outlet port structured and arranged to connect to an air delivery tube configured to pass the pressurised flow of breathable gas to a patient interface. The pivotable outlet port is able to pivot about at least one axis.

Another aspect of the present technology relates to a pivotable outlet port configured to pneumatically connect a flow generator to an air delivery tube. The pivotable outlet port includes an outlet portion pivotally coupled to the flow generator and adapted to interface with the air delivery tube, an inlet portion adapted to interface with the flow generator (or water reservoir dock), and a decoupling portion that connects the inlet portion to the outlet portion. The decoupling portion is structured and arranged to decouple pivotal movement of the outlet portion from the inlet portion.

Another aspect of the present technology relates to an apparatus for humidifying a flow of breathable gas including a water reservoir including a cavity structured to hold a volume of water, a water reservoir dock structured and arranged to receive the water reservoir in an operative position, an air delivery tube configured to pass the flow of breathable gas that has been humidified in the water reservoir to a patient interface, and a pivotable outlet port provided to the water reservoir dock. The pivotable outlet port is configured to pneumatically connect the water reservoir to the air delivery tube. The pivotable outlet port includes an outlet portion pivotally coupled to the water reservoir dock and adapted to interface with the air delivery tube, an inlet portion adapted to interface with the water reservoir, and a decoupling portion that connects the inlet portion to the outlet portion. The decoupling portion is structured and arranged to decouple pivotal movement of the outlet portion from the inlet portion.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

4.2 Patient Interface

FIG. 2 shows a patient interface in the form of a nasal mask in accordance with one form of the present technology.

4.3 RPT Device and Humidifier

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

Figure 1:
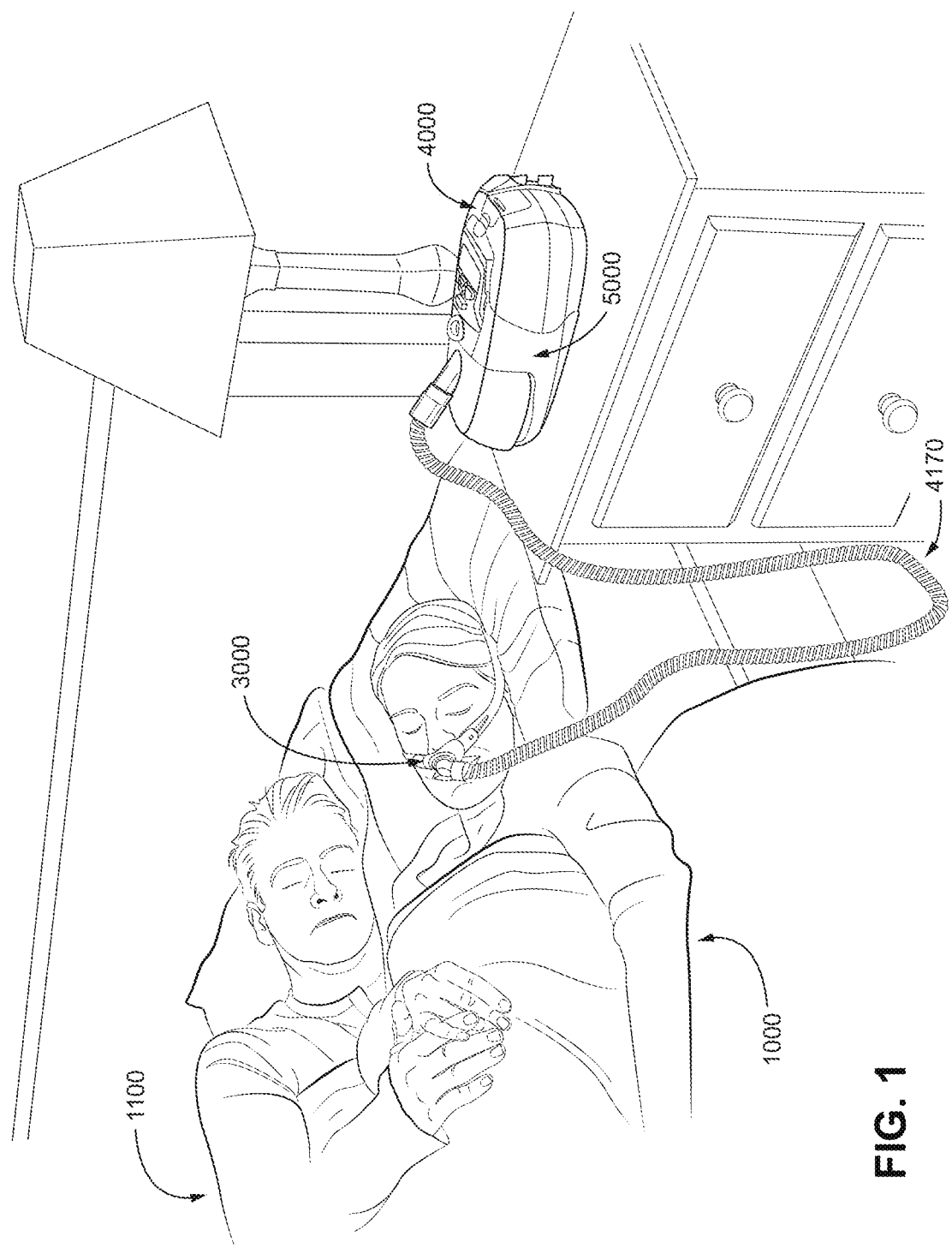

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000, e.g., see FIG. 1.

5.3 Patient Interface

Figure 2:
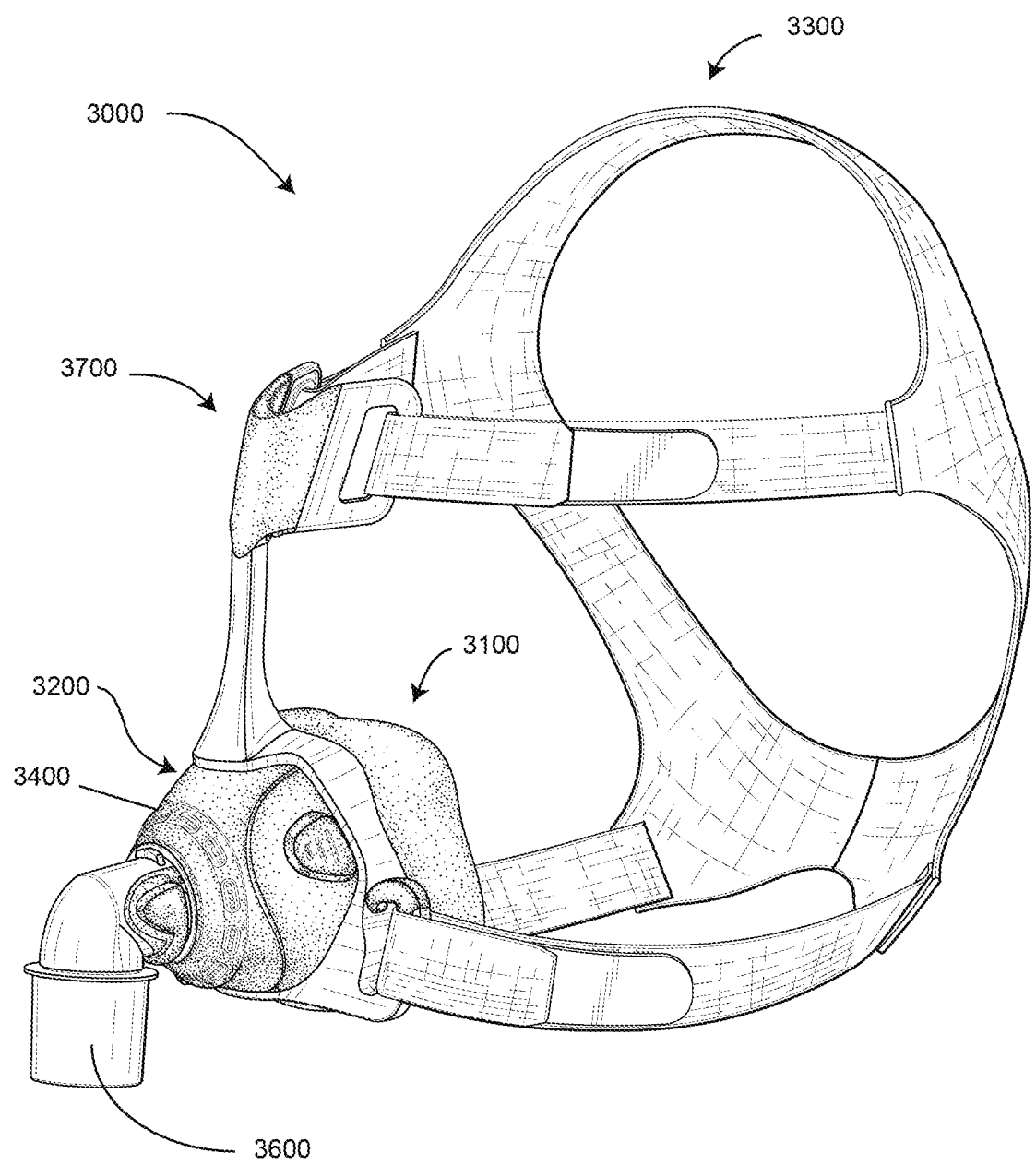

FIG. 2 shows a non-invasive patient interface 3000 in accordance with one aspect of the present technology comprising the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient. The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.4 RPT Device

Figure 3A:
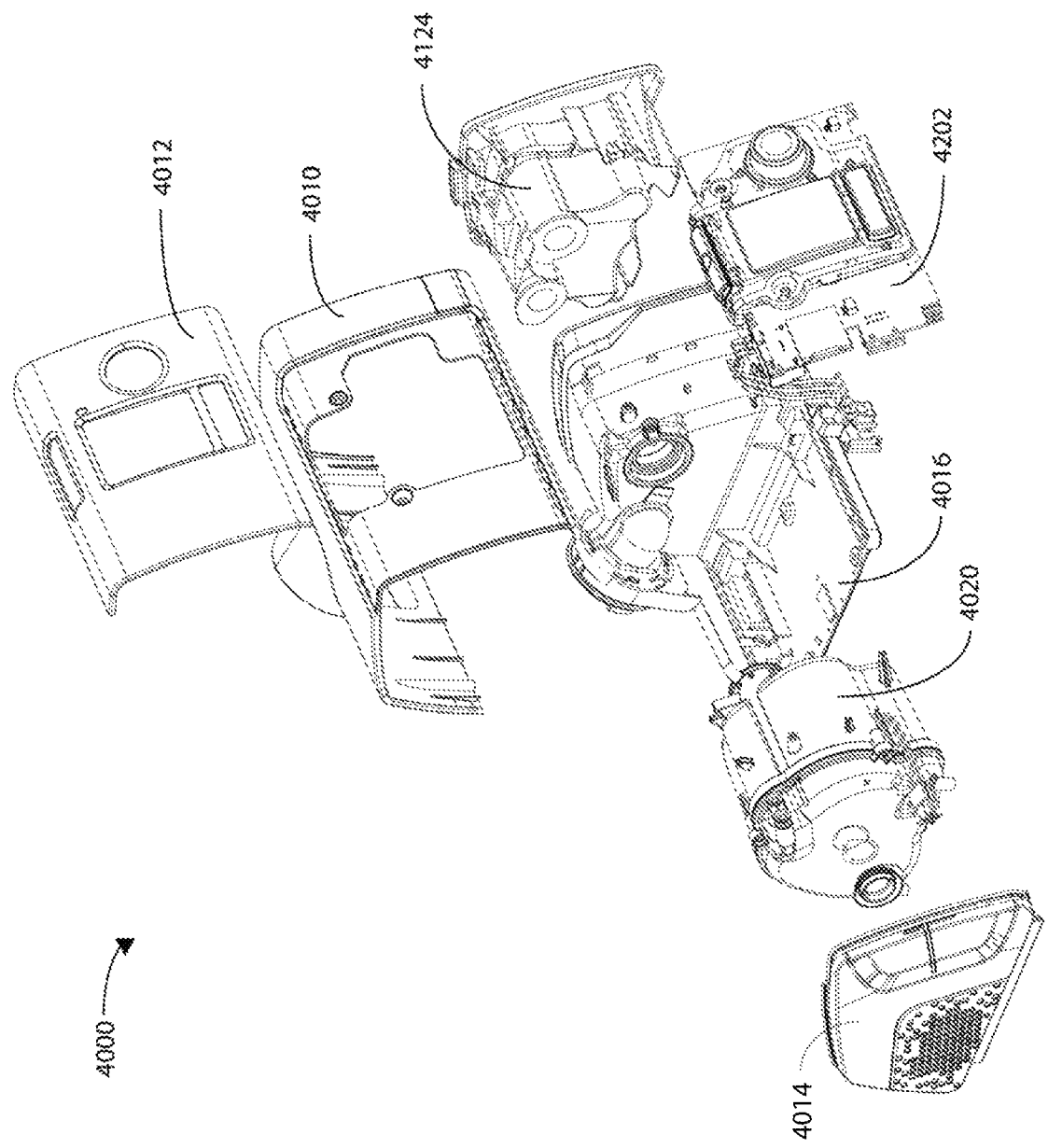
FIG. 3A is an exploded perspective view of an RPT device 4000 in accordance with one form of the present technology.

An exploded view of an RPT device 4000 in accordance with one aspect of the present technology is shown in FIG. 3A. An RPT device 4000 may comprise mechanical, pneumatic, and/or electrical components and be configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10 cmH$_2$O, or at least 20 cmH$_2$O.

Figure 3B:
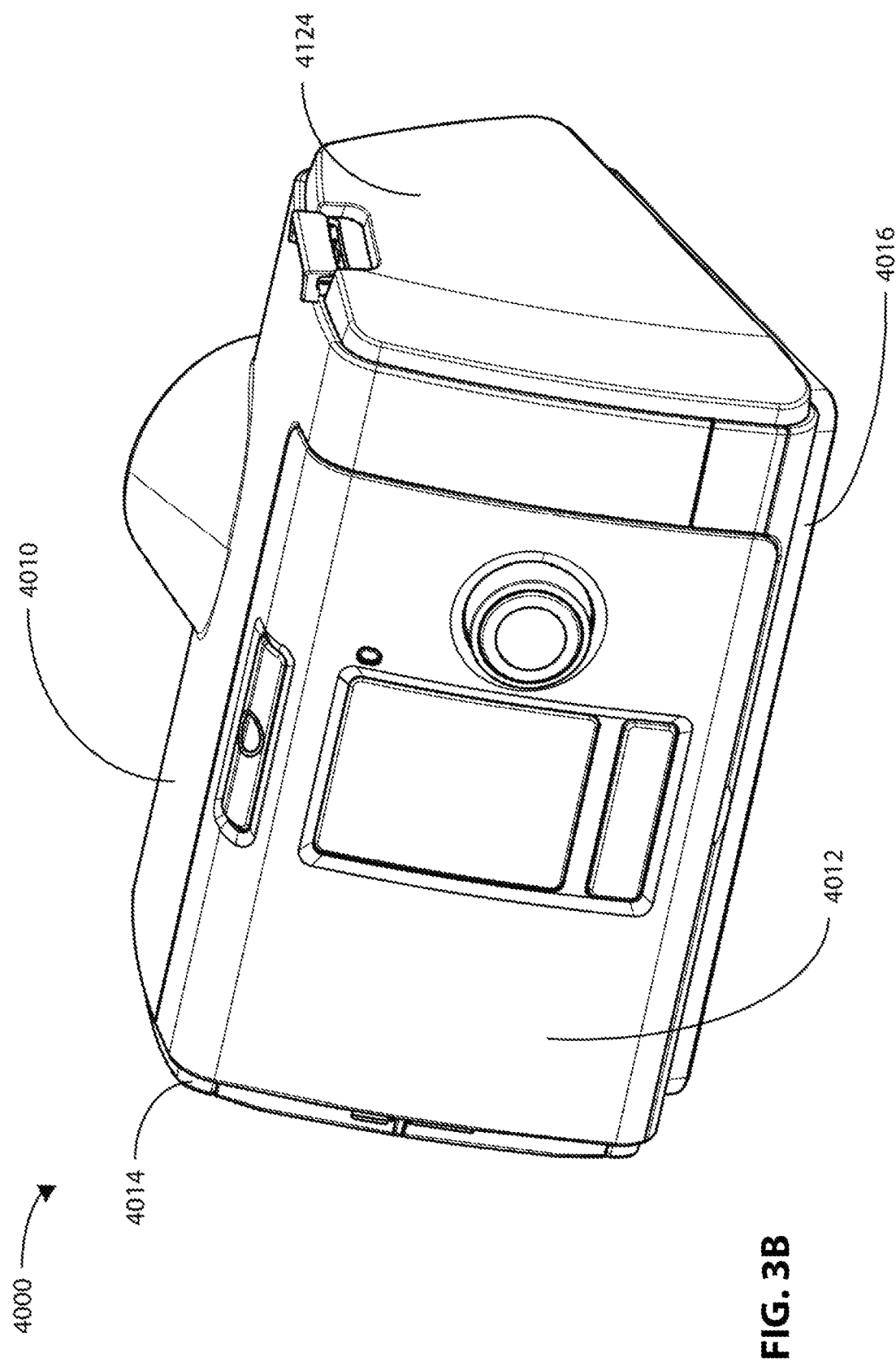
FIG. 3B is a perspective view of an RPT device 4000 comprising an outlet muffler 4124 in accordance with one form of the present technology.
Figure 3C:
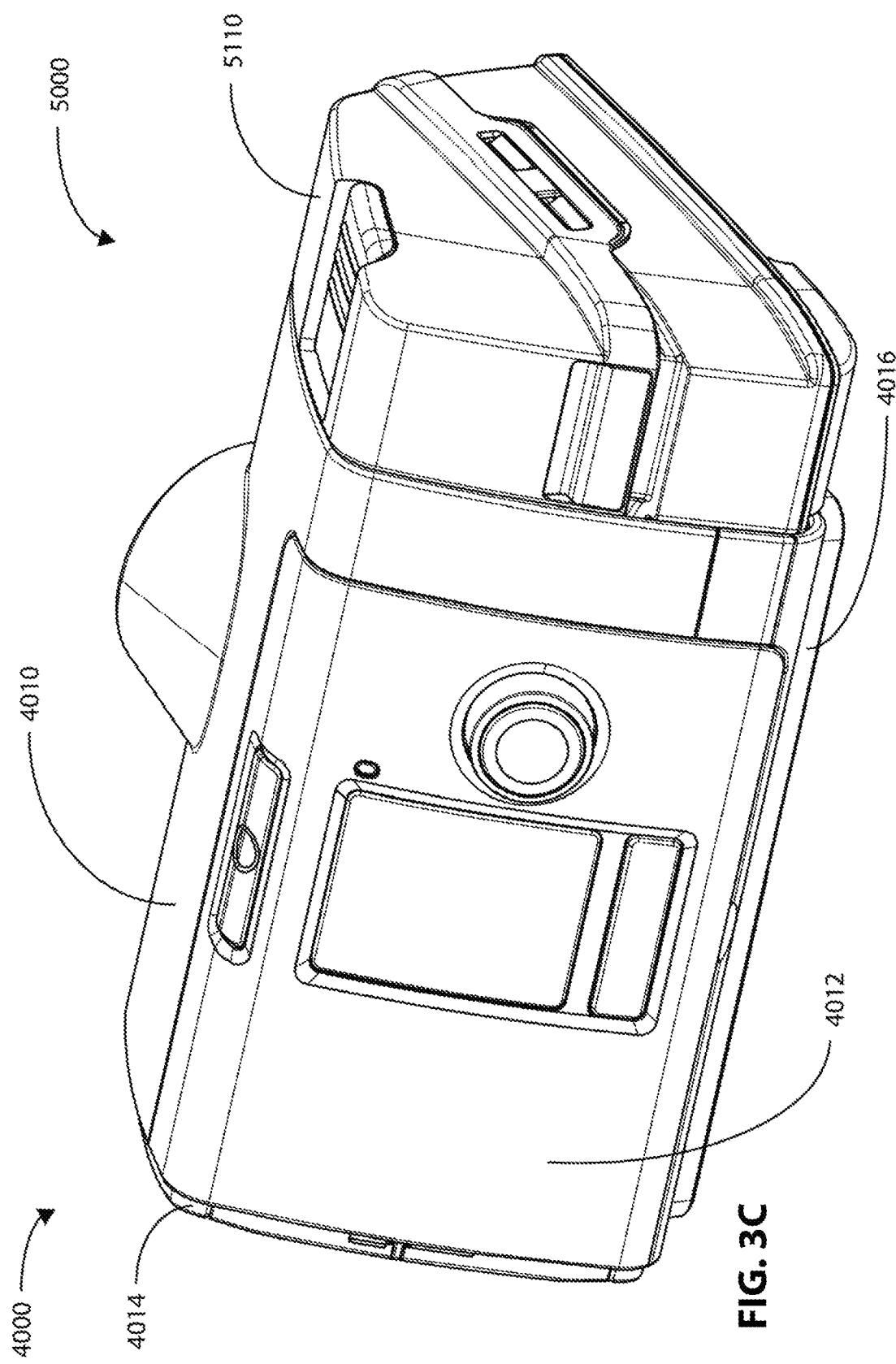
FIG. 3C is a perspective view of an RPT device 4000 with an integrated humidifier 5000 comprising a water reservoir 5110 in accordance with one form of the present technology.
Figure 3D:
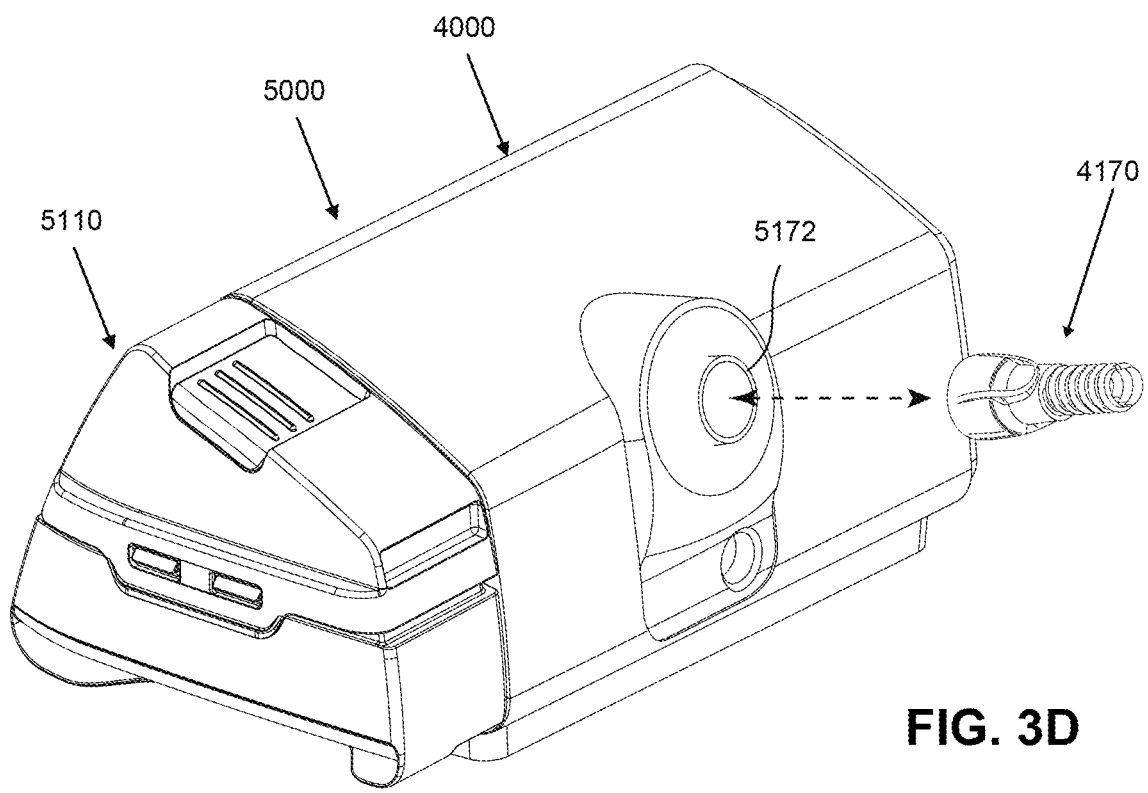
FIG. 3D is a perspective view of an RPT device 4000 with an integrated humidifier 5000 according to an example of the present technology, and demonstrating engagement with the air circuit 4170 according to an example of the present technology.

The RPT device 4000 may include an external housing having one or more panel(s) such as a main panel 4010, a front panel 4012 and a side panel 4014. The RPT device 4000 may also comprise an outlet muffler 4124 as shown in FIGS. 3A and 3B. The outlet muffler 4124 may be removable and replaced with a water reservoir 5110 (see FIGS. 3C to 3E). In such forms, the RPT device 4000 may be considered to include an integrated humidifier 5000. Thus, the RPT device 4000 may be used with or without humidification depending upon whether the water reservoir 5110 or the outlet muffler 4124 respectively is attached. Preferably the RPT device 4000 comprises a chassis 4016 that supports one or more internal components of the RPT device 4000. In one form the RPT device 4000 comprises a pressure generator, which may be housed in a pneumatic block 4020 coupled to the chassis 4016.

Electrical components may be mounted on a single Printed Circuit Board Assembly (PCBA) 4202. In an alternative form, the RPT device 4000 may include more than one PCBA 4202.

Further examples and details of an exemplary RPT device are described in PCT Publication No. WO 2015/089582, which is incorporated herein by reference in its entirety.

A power supply may be located internal or external of the external housing 4010 of the RPT device 4000.

In one form of the present technology, power supply provides electrical power to the RPT device 4000 only. In another form of the present technology, power supply provides electrical power to both RPT device 4000 and humidifier 5000.

In one form of the present technology, the RPT device includes a central controller including one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller is a dedicated electronic circuit.

In one form, the central controller is an application-specific integrated circuit. In another form, the central controller comprises discrete electronic components.

The central controller may be configured to receive input signal(s) from one or more transducers, one or more input devices, and the humidifier 5000.

The central controller may be configured to provide output signal(s) to one or more of an output device, a therapy device controller, a data communication interface, and the humidifier 5000.

In some forms of the present technology, the central controller is configured to implement the one or more methodologies described herein, such as the one or more algorithms expressed as computer programs stored in a non-transitory computer readable storage medium, such as memory. In some forms of the present technology, the central controller may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, is delivered to one or more points in the pneumatic path, such as upstream of the pneumatic block 4020, to the air circuit 4170, and/or to the patient interface 3000.

5.6 Humidifier

5.6.1 Humidifier Overview

In one form of the present technology there is provided a humidifier 5000 (e.g. as shown in FIGS. 3C to 3F) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

FIGS. 3C to 3F show a RPT device 4000 with an integrated humidifier 5000 according to an example of the present technology. In the illustrated example, the humidifier 5000 includes a water reservoir dock 5130 structured to receive a water reservoir 5110. As shown, the water reservoir dock 5130 includes a cavity 5160 formed therein to receive the water reservoir 5110, e.g., the water reservoir 5110 may be insertable/removable from the water reservoir dock 5110 in a lateral direction.

Figure 3E:
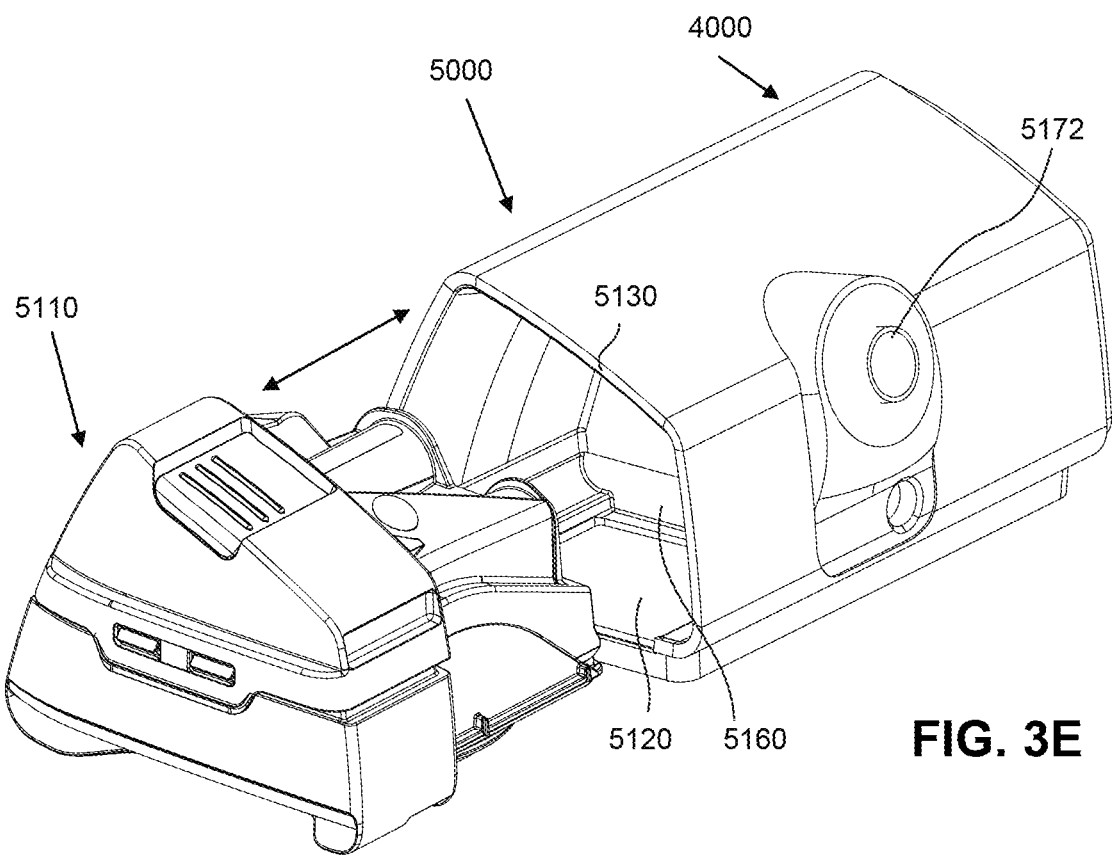
FIG. 3E is a perspective view of the integrated RPT device and humidifier of FIG. 3D demonstrating engagement of the water reservoir 5110 with the reservoir dock 5130 according to an example of the present technology.
Figure 3F:
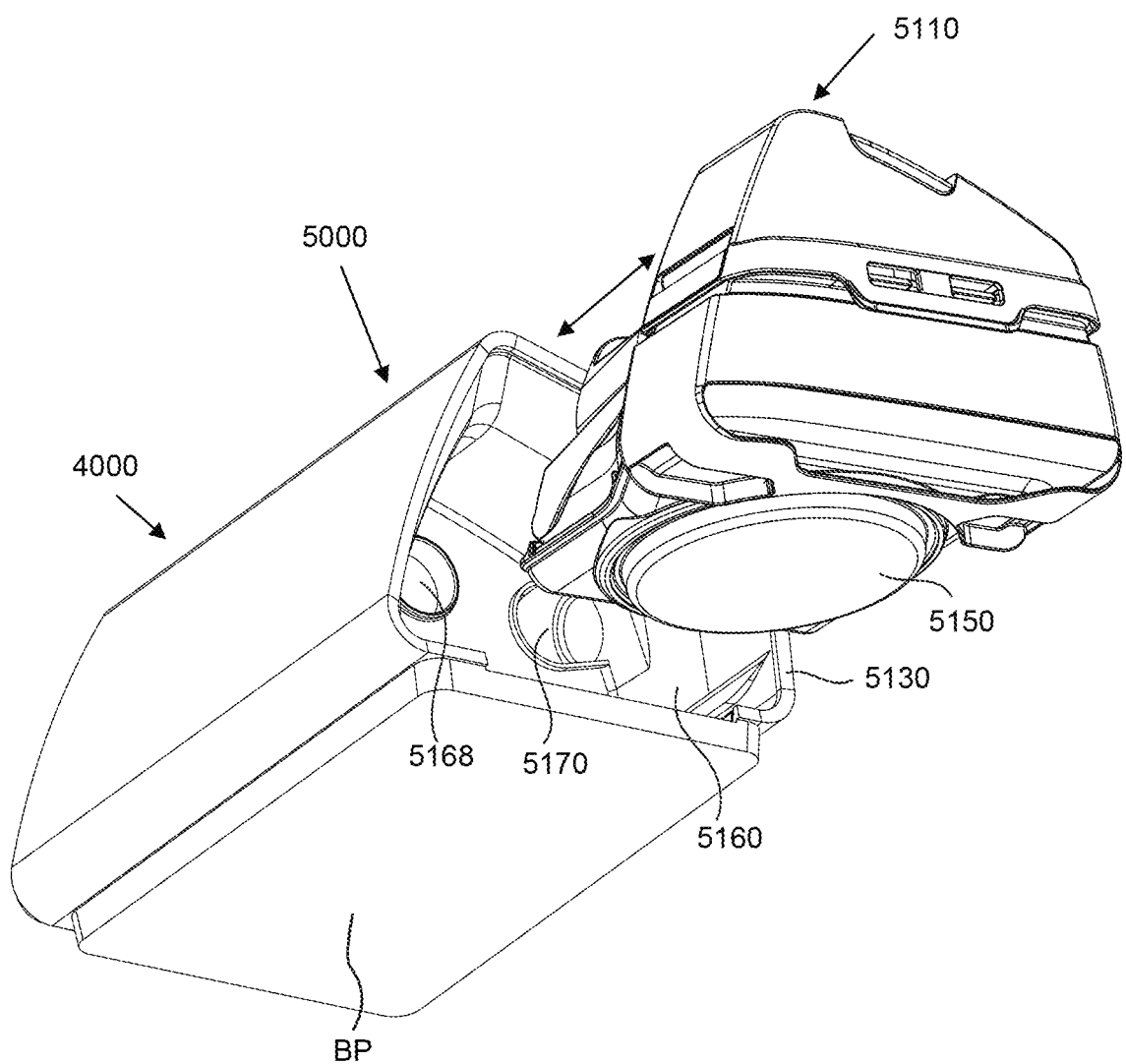
FIG. 3F is another perspective view of the integrated RPT device and humidifier of FIG. 3D demonstrating engagement of the water reservoir 5110 with the reservoir dock 5130 according to an example of the present technology.

In the illustrated example, the RPT device 4000 is integrated with the humidifier 5000. In this arrangement, the water reservoir dock 5130 is structured to connect the water reservoir 5110 to the pneumatic path. As best shown in FIGS. 3E and 3F, the reservoir dock 5130 comprises a dock air outlet 5168 to deliver a flow of air to the water reservoir 5110, a dock air inlet 5170 to receive the flow of air that has been humidified in the water reservoir 5110, and a humidifier outlet 5172 to transfer the flow of humidified air to the air circuit 4170. The cavity 5160 may include a top portion configured to cover at least a portion of the lid of the water reservoir 5110 and a bottom portion including a heater plate 5120.

However, it should be appreciated that the reservoir dock 5130 may be provided separately to RPT device 4000 in an alternative arrangement. In such an arrangement, additional interfaces may be used to connect the reservoir dock 5130 to the RPT device 4000, e.g., directly coupled or coupled via an air circuit.

In another arrangement, the water reservoir dock 5130 may comprise an opening in a substantially horizontal plane, so that the water reservoir 5110 may be inserted from above or below the water reservoir dock 5130.

Further examples and details of such RPT device 4000 and integrated humidifier 5000 are described in PCT Publication No. WO 2014/138804, published Sep. 18, 2014, which is incorporated herein by reference in its entirety.

5.6.2 Humidifier Components

5.6.2.1 Water Reservoir

FIGS. 3C to 3F show a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 3E and FIG. 3F. The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIGS. 3C to 3F) configured to receive the humidifier reservoir 5110. In some arrangements, the humidifier reservoir dock 5130 may comprise a locking feature such as a locking lever configured to retain the reservoir 5110 in the humidifier reservoir dock 5130.

Air Delivery Tube to Reservoir Dock Connection

FIGS. 5 to 16 illustrate an integrated RPT device and humidifier 6000 including a pivotable outlet port 6500 according to an example of the present technology. As illustrated, the integrated RPT device and humidifier 6000 includes a reservoir dock 6050 that is structured and arranged to receive a water reservoir (also referred to as a humidifier tub or a humidifier reservoir), e.g., see FIGS. 3C to 3F. In an example, the water reservoir may be removable and replaced with an outlet muffler, e.g., see FIGS. 3A and 3B described above. Thus, in an example, the integrated RPT device and humidifier 6000 may be used with or without humidification depending upon whether a water reservoir or an outlet muffler respectively is attached to the reservoir dock 6050.

In the example, the pivotable outlet port 6500 is provided to the dock outlet 6090 of the reservoir dock 6050 to pneumatically connect a water reservoir or outlet muffler to the air delivery tube 4170. The pivotable outlet port 6500 is configured to deliver pressurized air that has been humidified in the water reservoir, or that has passed through the outlet muffler, to the air delivery tube 4170. In an example, the pivotable outlet port 6500 may also at least partially locate and secure the air delivery tube 4170 to the reservoir dock 6050. Whilst described in the context of an RPT device with an integrated humidifier, the pivotable nature of the described outlet port is not directly associated with the humidification of the provided air. The function of the outlet port is to conveniently pass on the pressurized air generated in the RPT device to the air circuit 4170 and the patient interface 3000. As such, the described pivotable outlet port 6500 may even be used with an RPT device without a humidifier. Thus, the pivotable outlet port 6500 may be located anywhere on the integrated RPT device and/or humidifier 6000.

As best shown in FIGS. 5 to 8, the pivotable outlet port 6500 comprises an outlet portion 6510 pivotally coupled to the reservoir dock 6050 and adapted to interface with the air delivery tube 4170, an inlet portion 6530 adapted to interface with the water reservoir or outlet muffler, and a decoupling portion 6550 that provides a decoupling connection between the inlet portion 6530 to the outlet portion 6510. The decoupling portion 6550 is structured and arranged to allow movement of the outlet portion 6510 relative to the inlet portion 6530, which allows the outlet portion 6510 to assume alternative positions or orientations relative to the reservoir dock 6050 for connection to the air delivery tube 4170 without impacting the inlet portion 6530 and its interface with the water reservoir, outlet muffler or other components of the RPT device, i.e., by decoupling movement of the outlet portion 6510 from the inlet portion 6530, decoupling portion 6550 effectively decouples movement of the air delivery tube 4170 from its physical connection to the RPT device and/or the humidifier associated with it, at least with respect to a pivotal movement around one or more axes.

Figure 7:
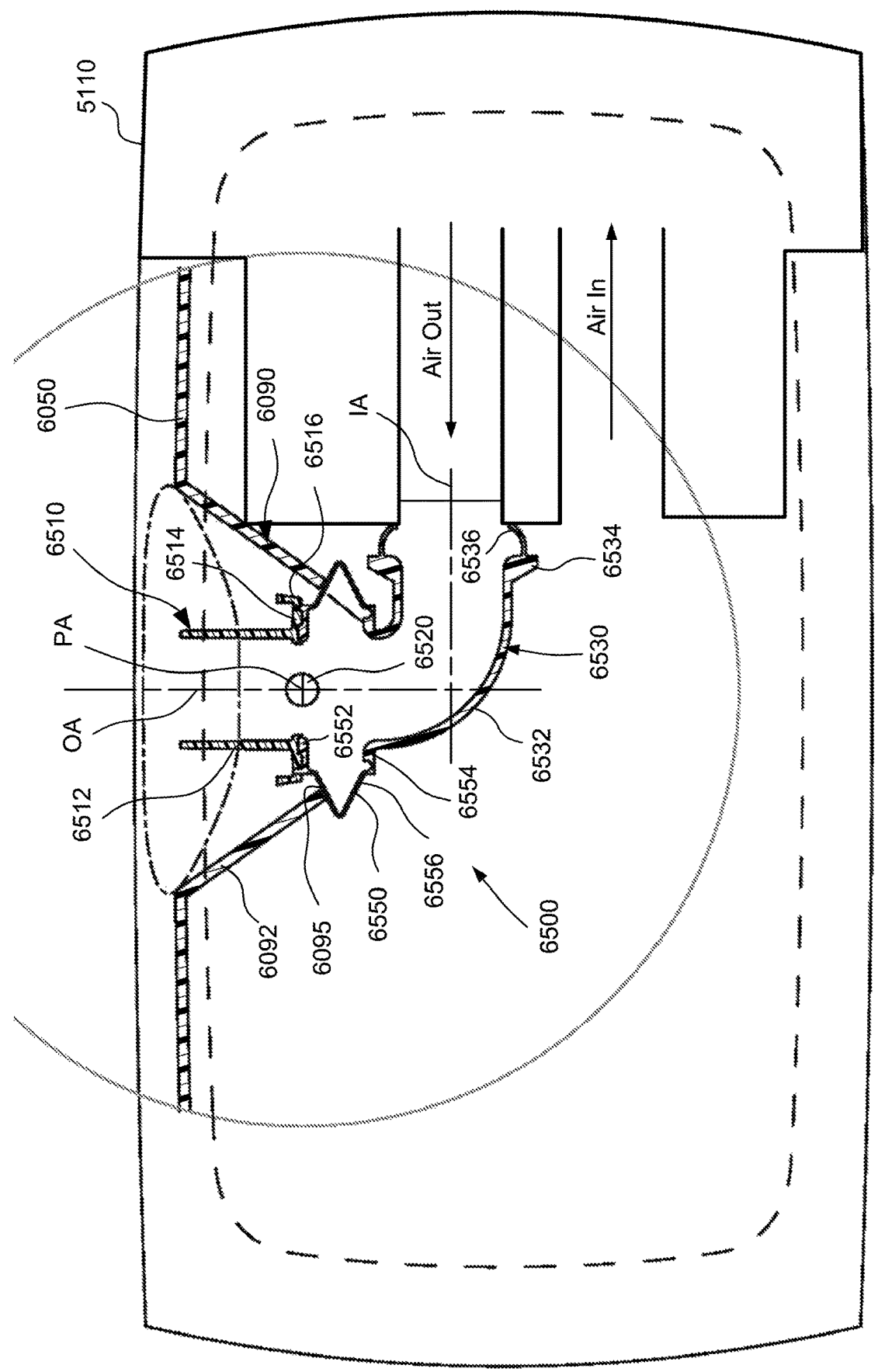
FIG. 7 is another cross-sectional view showing the pivotable outlet port of FIG. 5 at the dock outlet of the integrated RPT device and humidifier.
Figure 8:
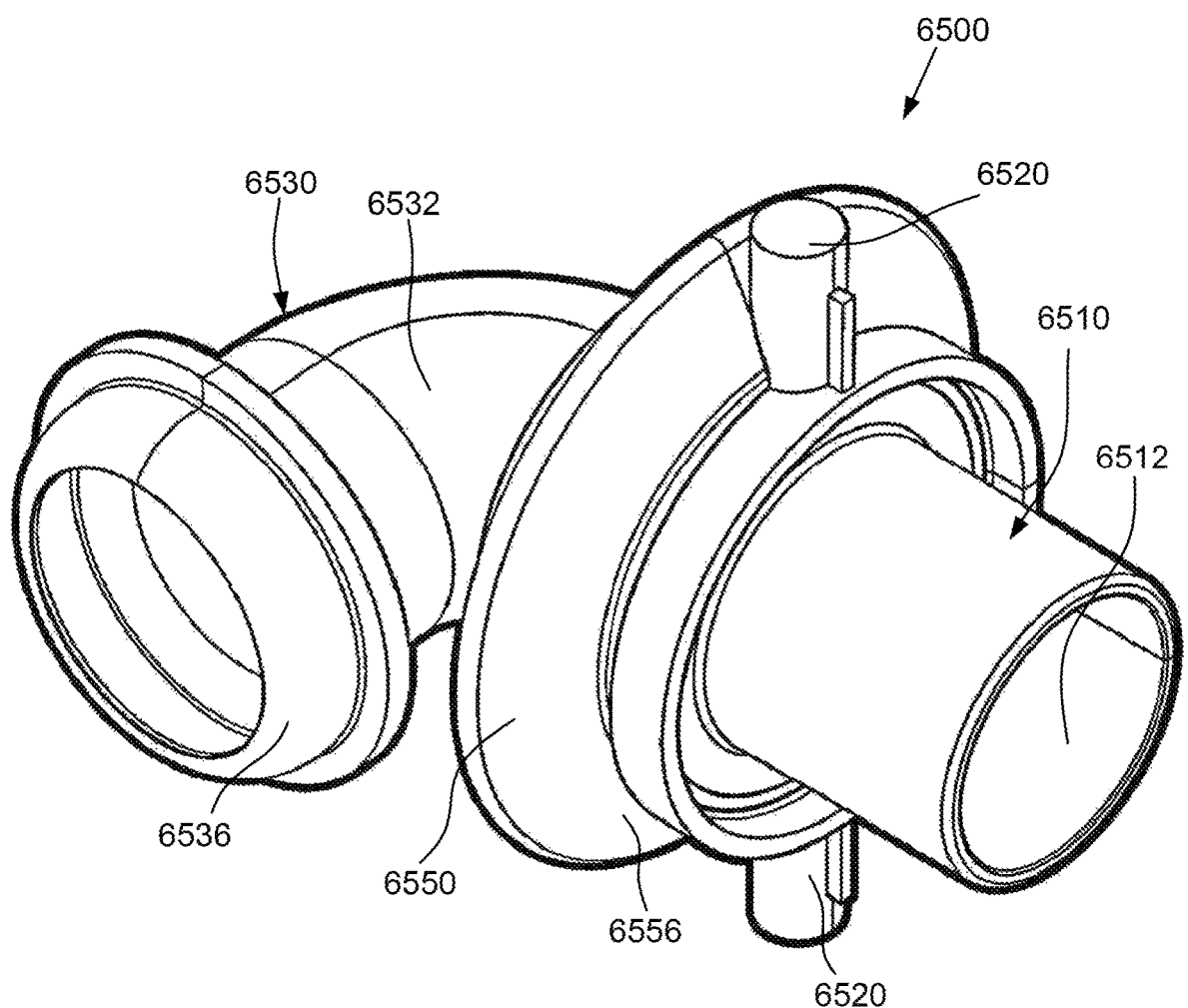
FIG. 8 is a perspective view of a pivotable outlet port according to an example of the present technology.

As best shown in FIG. 7, in the illustrated example, the outlet portion 6510 includes an outlet tube 6512, a flange 6514 arranged at a free end of the outlet tube 6512, and an end wall 6516 arranged along the outer perimeter of the flange 6514. In an example, the outlet tube 6512 may comprise an ISO taper, e.g., 22 mm outer diameter ISO taper, for coupling to the air delivery conduit 4170. In an example, the end wall 6516 may be coaxial with the outlet tube 6512.

Figure 5:
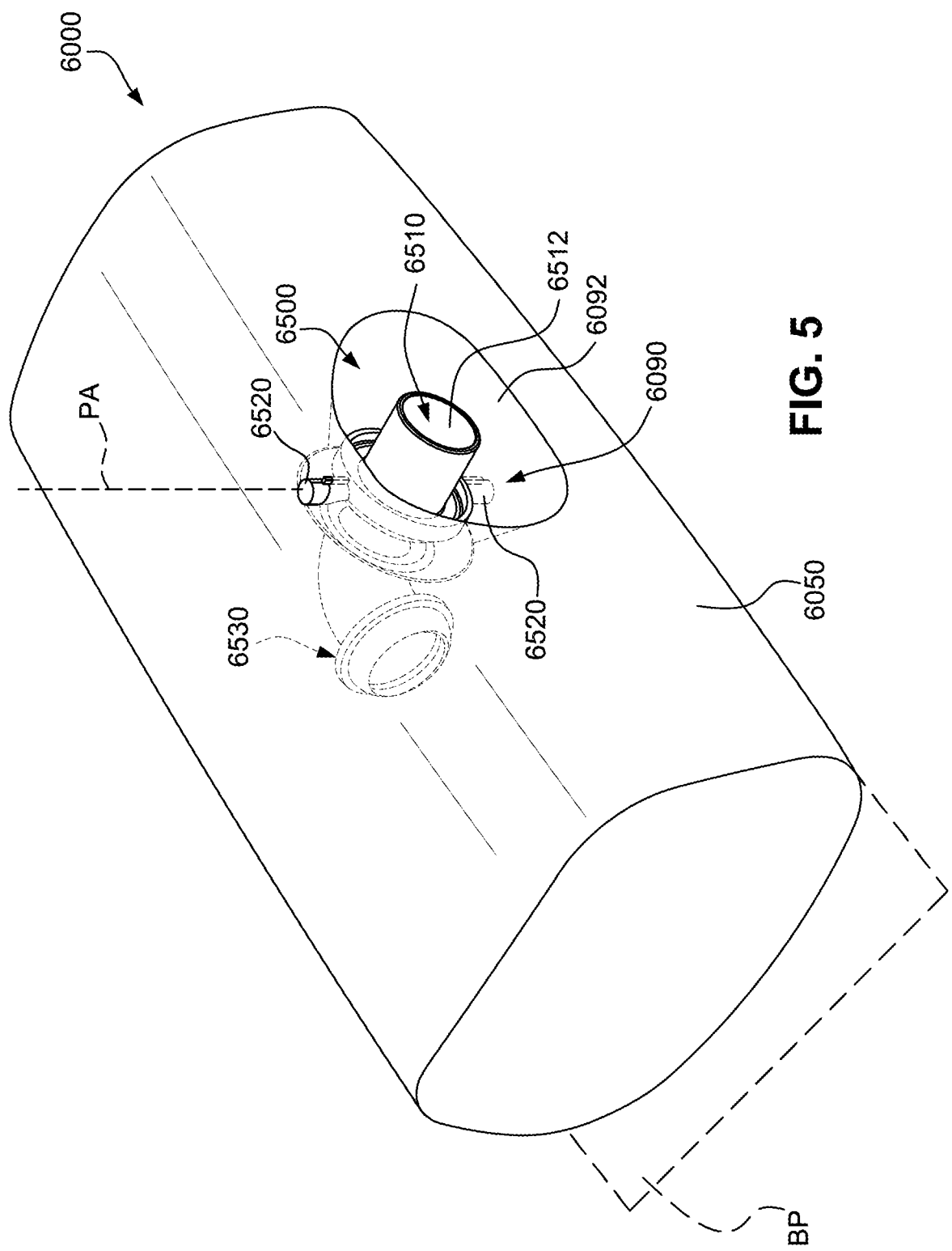
FIG. 5 is a perspective view of an integrated RPT device and humidifier including a pivotable outlet port according to an example of the present technology.
Figure 6:
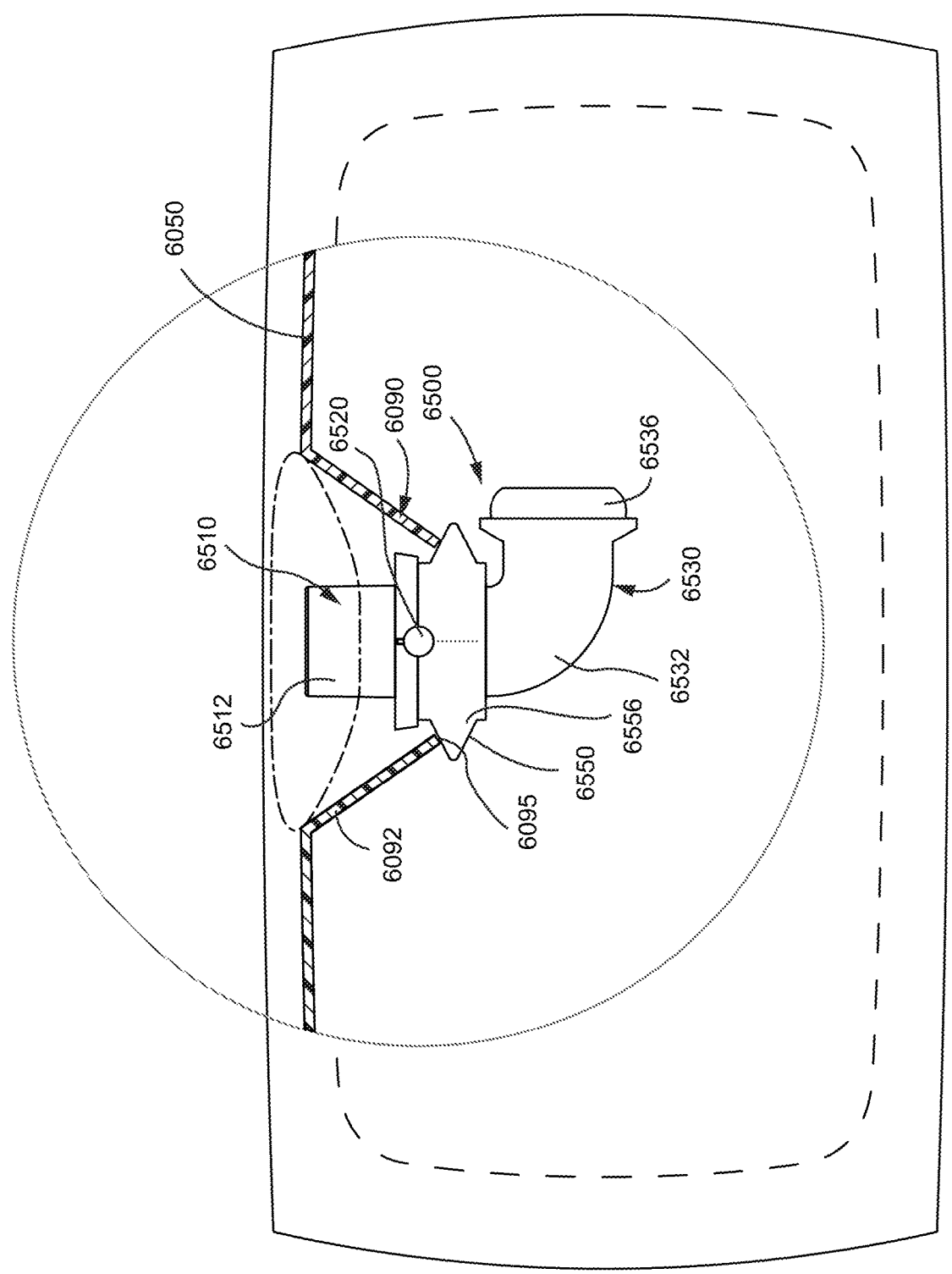
FIG. 6 is a cross-sectional view showing the pivotable outlet port of FIG. 5 at the dock outlet of the integrated RPT device and humidifier.

In addition, a single pin or a pair of opposed, protruding, and cylindrical pivot pins 6520 extend from the outlet tube 6512 (e.g., at superior and inferior sides of the outlet tube 6512) for forming a pivot or hinge connection with the reservoir dock 6050. As shown in FIGS. 5 to 7, the dock outlet 6090 of the reservoir dock 6050 includes a tapered (e.g., inwardly converging) side wall 6092. The pivot pins 6520 are received within respective, opposed openings in the side wall 6092, which pivotally supports the outlet portion 6510 at the dock outlet 6090. The pivot or hinge connection allows the outlet portion 6510 to pivot relative to the reservoir dock 6050 about a single axis PA, e.g., about the axis of the pivot pins 6520.

As shown in FIGS. 5-16, the dock outlet 6090 is recessed with respect to an external wall of the apparatus. In particular, the dock outlet 6090 is located in a recessed wall cavity on any external wall of the apparatus so that no more than a portion of the outlet portion 6510 of the dock outlet protrudes outside the cavity and beyond the external wall of the apparatus. In some examples, the entire outlet portion 6510 fits within the cavity and no portion of the outlet portion 6510 protrudes beyond the external wall of the apparatus.

In the illustrated example, the integrated RPT device and humidifier 6000 includes a bottom surface defining a bottom plane BP (e.g., see FIGS. 3F and 5) that is substantially horizontal when the integrated RPT device and humidifier 6000 is in a working orientation. In an example, the outlet portion 6510 is pivotally connected to the reservoir dock 6050 such that axis PA is oriented vertically or generally perpendicular relative to the bottom plane BP and the pivoting movement is in a plane that is parallel to the bottom plane BP of the RPT and humidifier 6000.

FIG. 7 shows the back end of the pivoting arrangement, and its engagement with a water reservoir, such as the water reservoir 5110. The inlet portion 6530 includes an inlet tube 6532, a flange 6534 arranged at a free end of the inlet tube 6532, and an inlet seal 6536 protruding from the flange 6534 towards the inlet opening of the inlet tube 6532. In the illustrated example, the inlet tube 6532 is curved along its length. Depending on its length, the inlet portion of the inlet tube 6532 may define an axis IA that is substantially parallel to an insertion axis of the water reservoir or outlet muffler (e.g., the axis IA may also be substantially parallel to a longitudinal axis of the reservoir dock 6050) and may be substantially perpendicular to an axis OA of the outlet tube 6512 when the outlet portion 6510 is in its initial, rest position (e.g., see FIG. 7). When the water reservoir or outlet muffler is coupled to the reservoir dock 6050, the inlet seal 6536 is structured and arranged to engage and provide a seal with the outlet of the water reservoir or outlet muffler. The illustrated inlet seal 6536 comprises a bellows-type arrangement that may provide a certain degree of decoupling between the inlet portion 6530 and the water reservoir (or a respective outlet muffler). If the RPT device was designed with no separate humidification reservoir or respective outlet muffler in mind, the inlet portion 6530 would be engaging, in a similar manner, with the pneumatic block of the RPT device.

As best seen in FIG. 7, the decoupling portion 6550 in the illustrated example comprises a concertina or gusset arrangement including an outlet end 6552 connected to the outlet portion 6510, an inlet end 6554 connected to the inlet portion 6530, and a gusset or fold 6556 that interconnects the outlet and inlet ends 6552 and 6554. In the illustrated example, the decoupling portion 6550 includes a single gusset or fold 6556. However, it should be appreciated that the decoupling portion 6550 may have more than one fold. The gusset or fold 6556 comprises a flexible side wall that allows the gusset or fold to expand and/or contract when the outlet portion 6510 is pivoted relative to the reservoir dock 6050, which decouples such movement of the outlet portion 6510 from the inlet portion 6530. As shown in FIG. 7, the gusset or fold 6556 may include a generally triangular cross-section when not activated due to movement of the outlet portion 6510.

In the illustrated example, e.g., see FIG. 7, the outlet portion 6510 may comprise a first part or base mold constructed of a relatively rigid material (e.g., thermoplastic polymer (e.g., PC, ABS)) and the inlet portion 6530 and decoupling portion 6550 may comprise a second part or overmold constructed of a relatively soft and/or flexible material (e.g., thermoplastic elastomer (TPE) or silicone) that is provided (e.g., by overmolding) to the first part.

For example, as shown in FIG. 7, the inlet portion 6530 and the decoupling portion 6550 may comprise a one-piece construction (e.g., thermoplastic elastomer (TPE) or silicone), with the outlet end 6552 of the decoupling portion 6550 forming an overmolded connection to the flange 6514 of the outlet portion 6510. However, it should be appreciated that the inlet portion 6530 and the decoupling portion 6550 may be connected to the outlet portion 6510 in other suitable manners.

In an alternative example, each of the outlet portion 6510 and the inlet portion 6530 may comprise a relatively rigid material (e.g., thermoplastic polymer (e.g., PC, ABS)), and the decoupling portion 6550 may comprise a relatively soft and/or flexible material (e.g., thermoplastic elastomer (TPE) or silicone) that is overmolded to the outlet portion 6510 and the inlet portion 6530 to flexibly connect the outlet portion 6510 and the inlet portion 6530.

In an example, the pivotable outlet port 6500 may comprise a port, e.g., pressure port for measuring air pressure at the dock outlet 6090.

When the pivotable outlet port 6500 is connected to the dock outlet 6090 of the reservoir dock 6050, the outlet portion 6510 and outlet tube 6512 thereof protrudes out of the cavity of the reservoir dock 6050 to allow engagement with the air delivery tube 4170, e.g., see FIGS. 5 to 7. Likewise, the inlet portion 6530 and inlet seal 6536 thereof protrudes into the cavity of the reservoir dock 6050 to allow engagement with the water reservoir or outlet muffler. Further, when the outlet portion 6510 is in its initial, rest position, the gusset or fold 6556 of the decoupling portion 6550 is not activated and maintains the outlet tube 6512 so that it extends straight out the dock outlet 6090, i.e., the axis OA of the outlet tube 6512 extends generally as illustrated in FIGS. 7, 9, and 10.

Figure 9:
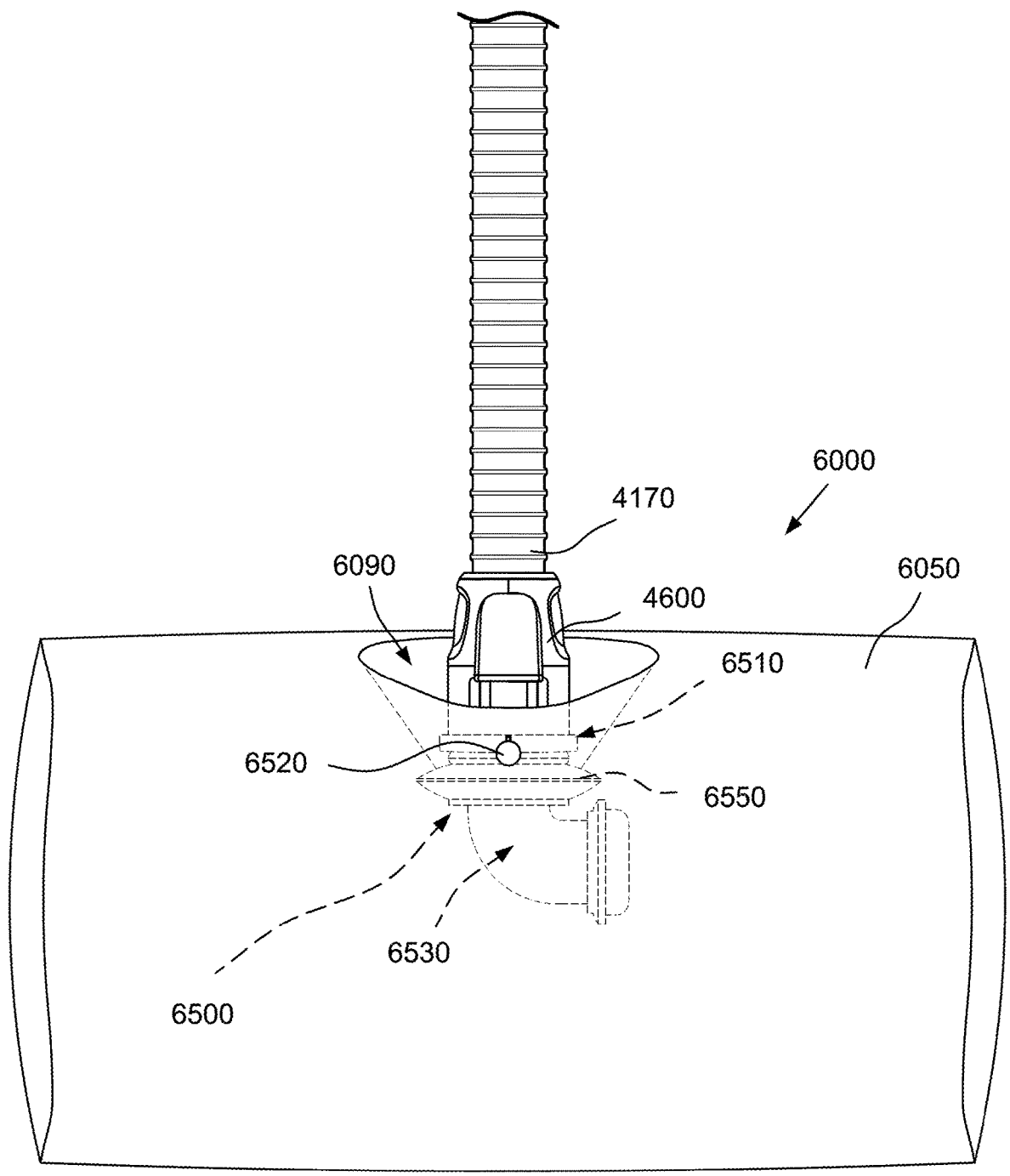
FIG. 9 is a top view showing air delivery tubing connected to the pivotable outlet port of the integrated RPT device and humidifier of FIG. 5.
Figure 10:
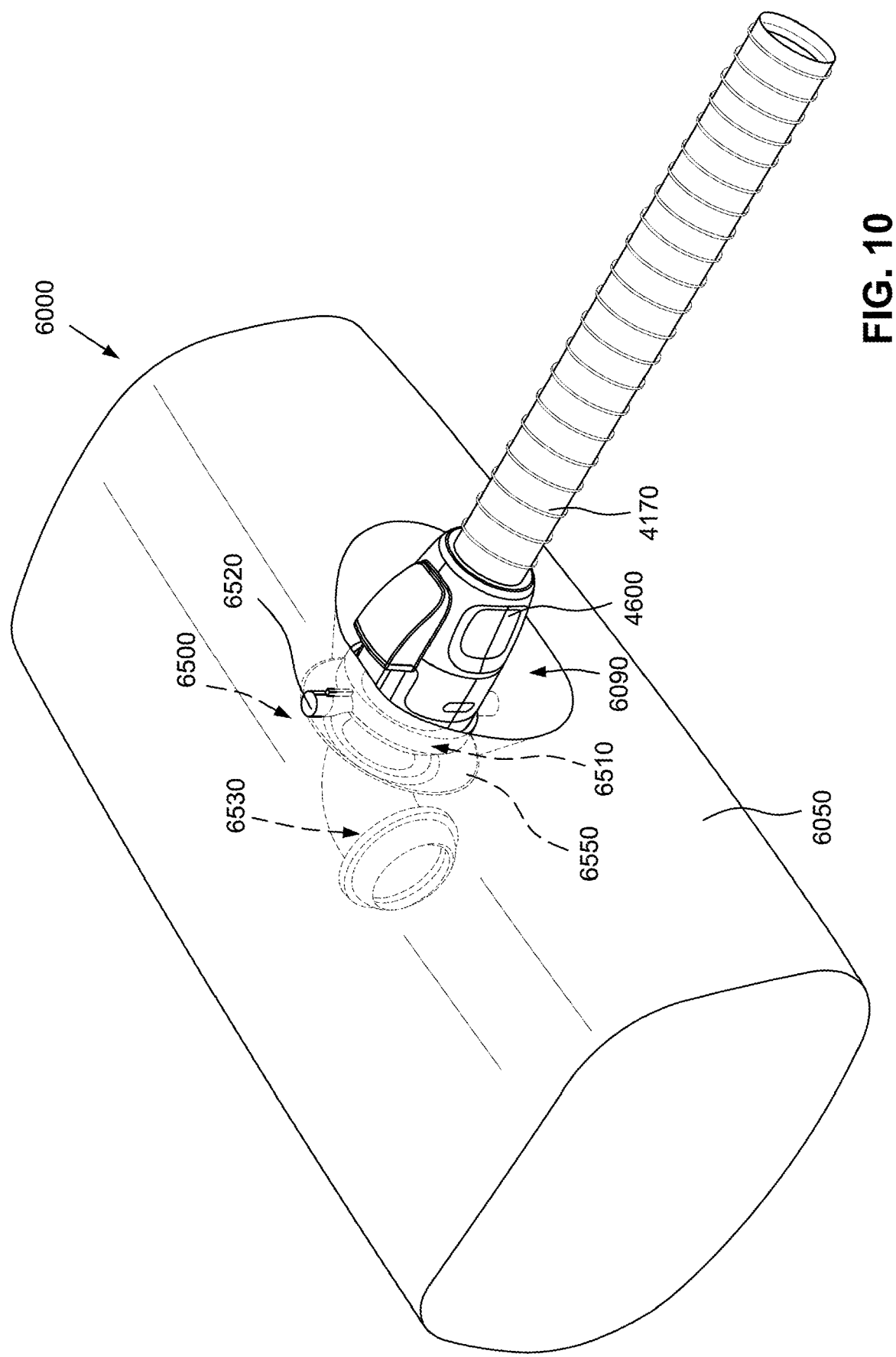
FIG. 10 is a perspective view showing air delivery tubing connected to the pivotable outlet port of the integrated RPT device and humidifier of FIG. 5.

FIGS. 9 and 10 illustrate engagement of a dock connector 4600 of the air delivery tube 4170 with the pivotable outlet port 6500 provided to the reservoir dock 6050. The dock connector 4600 is engaged with the pivotable outlet port 6500 so that the outlet tube 6512 extends into and engages the opening of the dock connector 4600. In an example, the dock connector 4600 may include a radial lip seal that is configured and arranged to engage against the exterior surface of the outlet tube 6512 so that a sealed, pneumatic connection is formed between the dock connector 4600 and the outlet tube 6512 of the pivotable outlet port 6500. In an example, the forward end of the dock connector 4600 may engage the flange 6514 of the outlet portion 6510 to indicate when the dock connector 4600 has reached an operative position and prevent further insertion of the outlet tube 6512 into the dock connector 4600.

When the dock connector 4600 is engaged with the pivotable outlet port 6500, the pivotable outlet port 6500 is structured and arranged to allow pivoting of the outlet portion 6510 and hence the attached air delivery tube 4170 within a horizontal plane that extends generally parallel to the bottom surface and bottom plane BP thereof of the integrated RPT device and humidifier 6000. That is, the outlet portion 6510 may be pivoted within the horizontal plane about its pivot axis PA to a maximum left position (as viewed in FIGS. 11 to 13), a maximum right position (as viewed in FIGS. 14 to 16), and any one of a plurality of intermediate positions between the maximum left and right positions.

In the illustrated example, the axis OA of the outlet tube 6512 in the maximum left position (as viewed in FIGS. 11 to 13) is oriented about −15° to −45°, e.g., −30°, from the axis OA of the outlet tube 6512 when in its initial, rest position (as viewed in FIGS. 5 to 10). Similarly, the axis OA of the outlet tube 6512 in the maximum right position (as viewed in FIGS. 14 to 16) is oriented about 15° to 45°, e.g., 30°, from the axis OA of the outlet tube 6512 when in its initial, rest position (as viewed in FIGS. 5 to 10). Accordingly, the outlet portion 6510 provides a range of movement between the maximum left and right positions of about 30° to 90°, e.g., 60°, in the illustrated example.

However, it should be appreciated that the outlet portion 6510 may include alternative ranges of movement, e.g., range of movement 0 to 180°, e.g., 20° to 140°, e.g., 40° to °120. In an example, the outlet portion 6510 may include a pivotal range of movement, in at least one plane associated with the apparatus, between the maximum left and right positions, within at least one of the following ranges: at least 30°, at least 90°, at least 180°, and at least 270°. If the outlet portion 6510 is arranged on a flat surface of a device, e.g., along a side of a device as illustrated in FIGS. 6 and 7, it is likely to exhibit a freedom of movement of up to 180°. However, if the outlet portion 6510 is arranged on a corner of a device, the freedom of movement may be up to 270°, and even beyond 270° if the corner defines less than a 90° angle.

Figure 11:
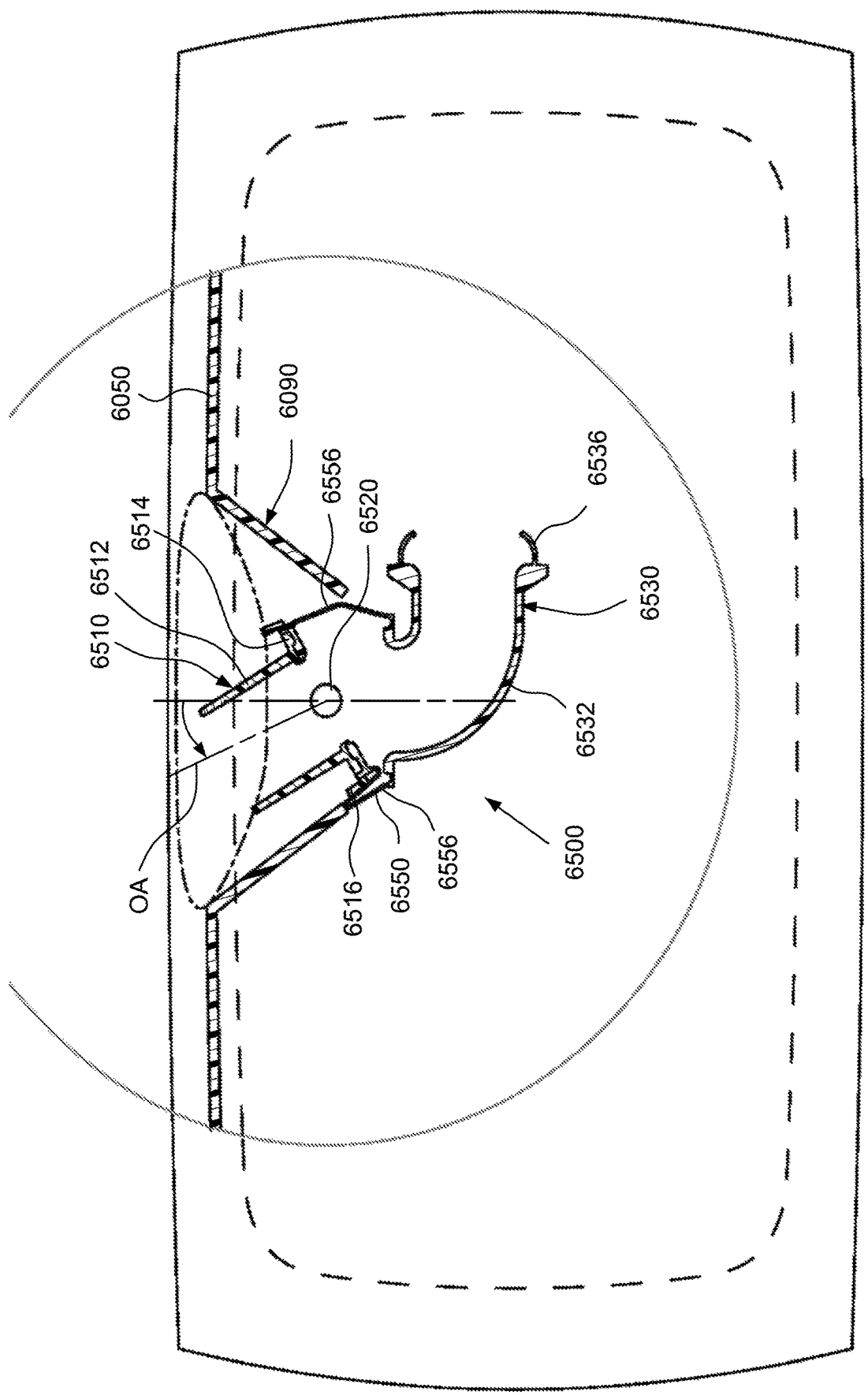
FIG. 11 is a cross-sectional view showing the pivotable outlet port of FIG. 5 with the outlet portion thereof pivoted to a maximum left position according to an example of the present technology.
Figure 12:
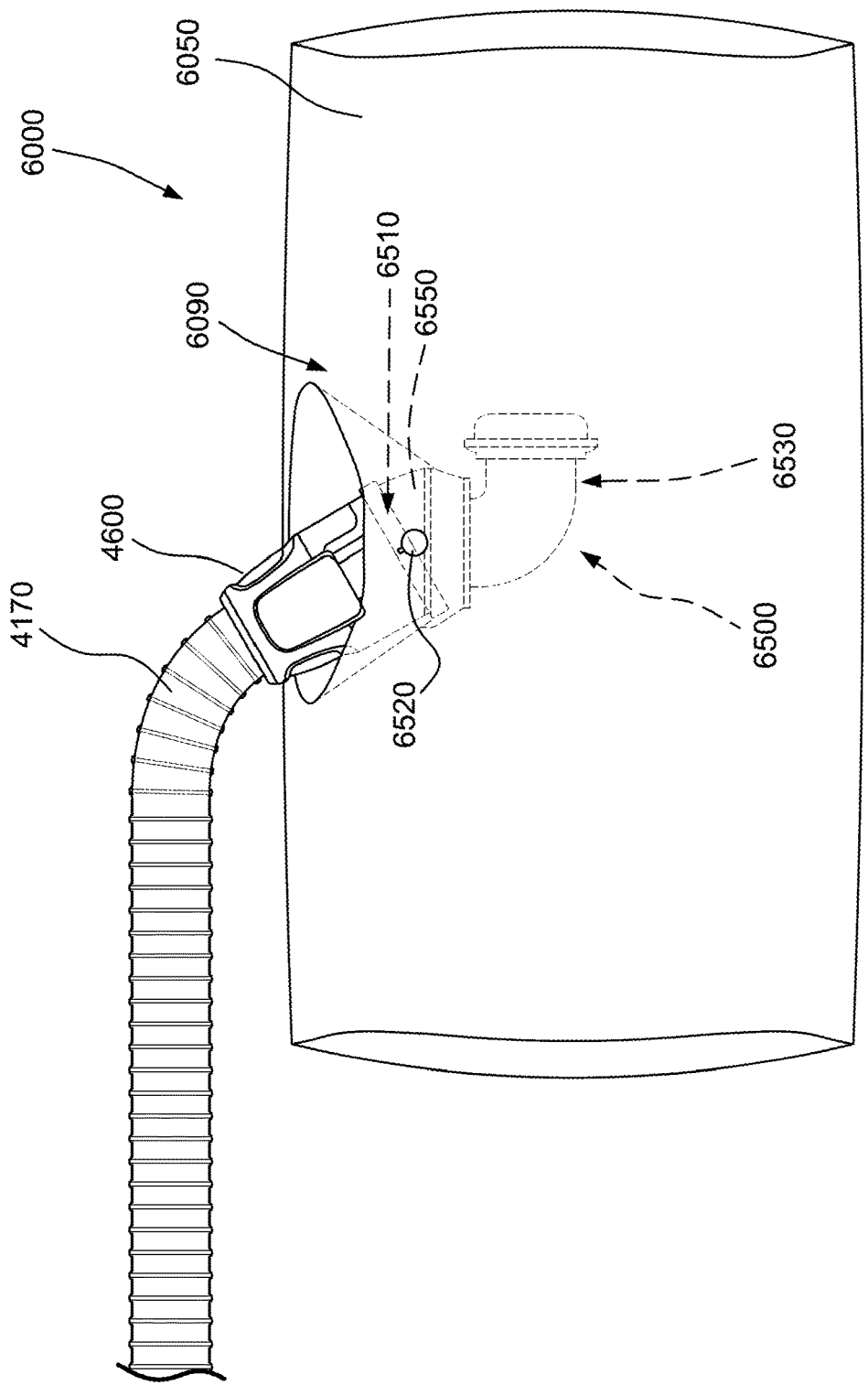
FIG. 12 is a top view showing air delivery tubing connected to the pivotable outlet port with the outlet portion thereof pivoted to the maximum left position of FIG. 11.
Figure 13:
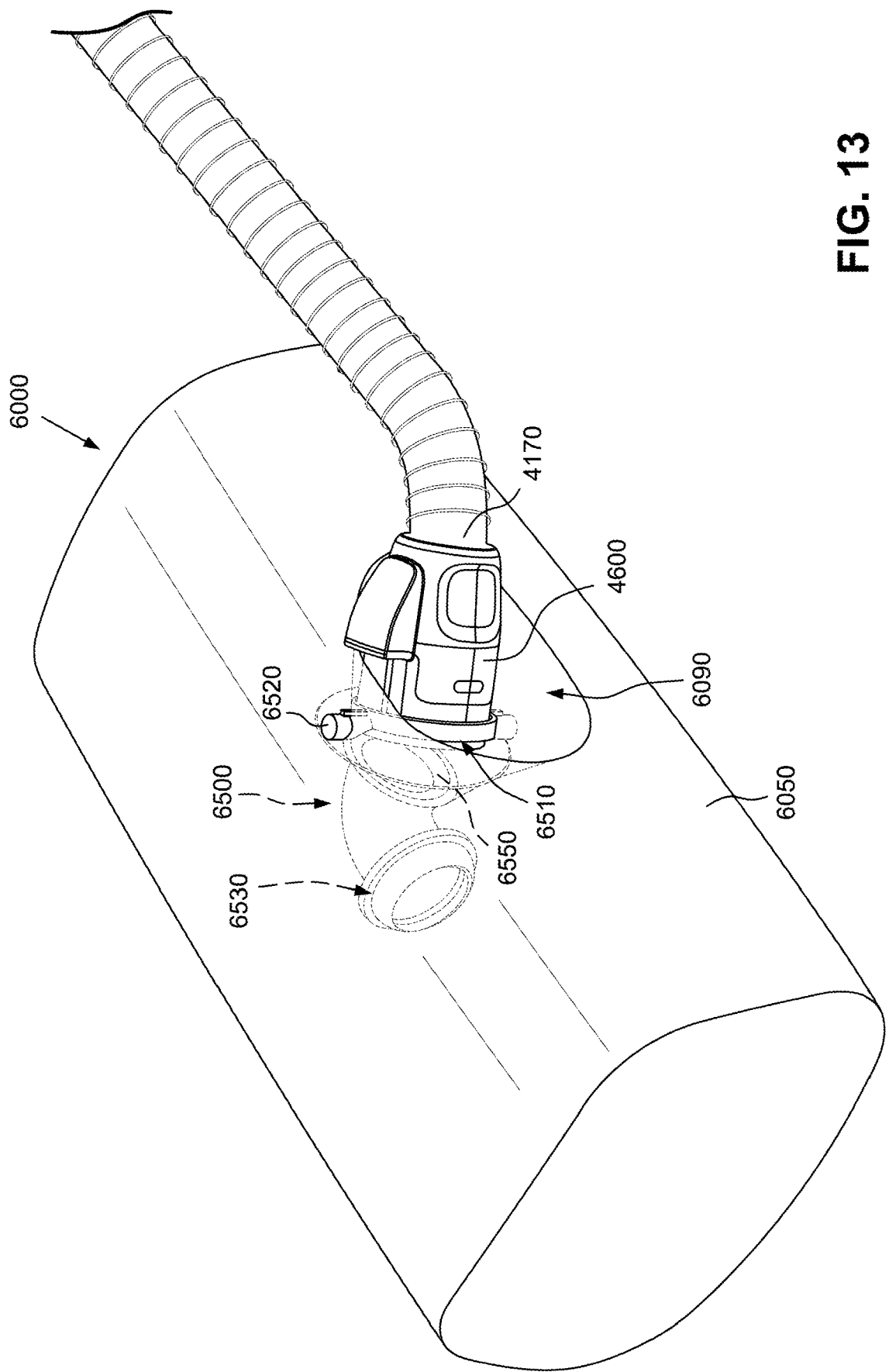
FIG. 13 is a perspective view showing air delivery tubing connected to the pivotable outlet port with the outlet portion thereof pivoted to the maximum left position of FIG. 11.
Figure 14:
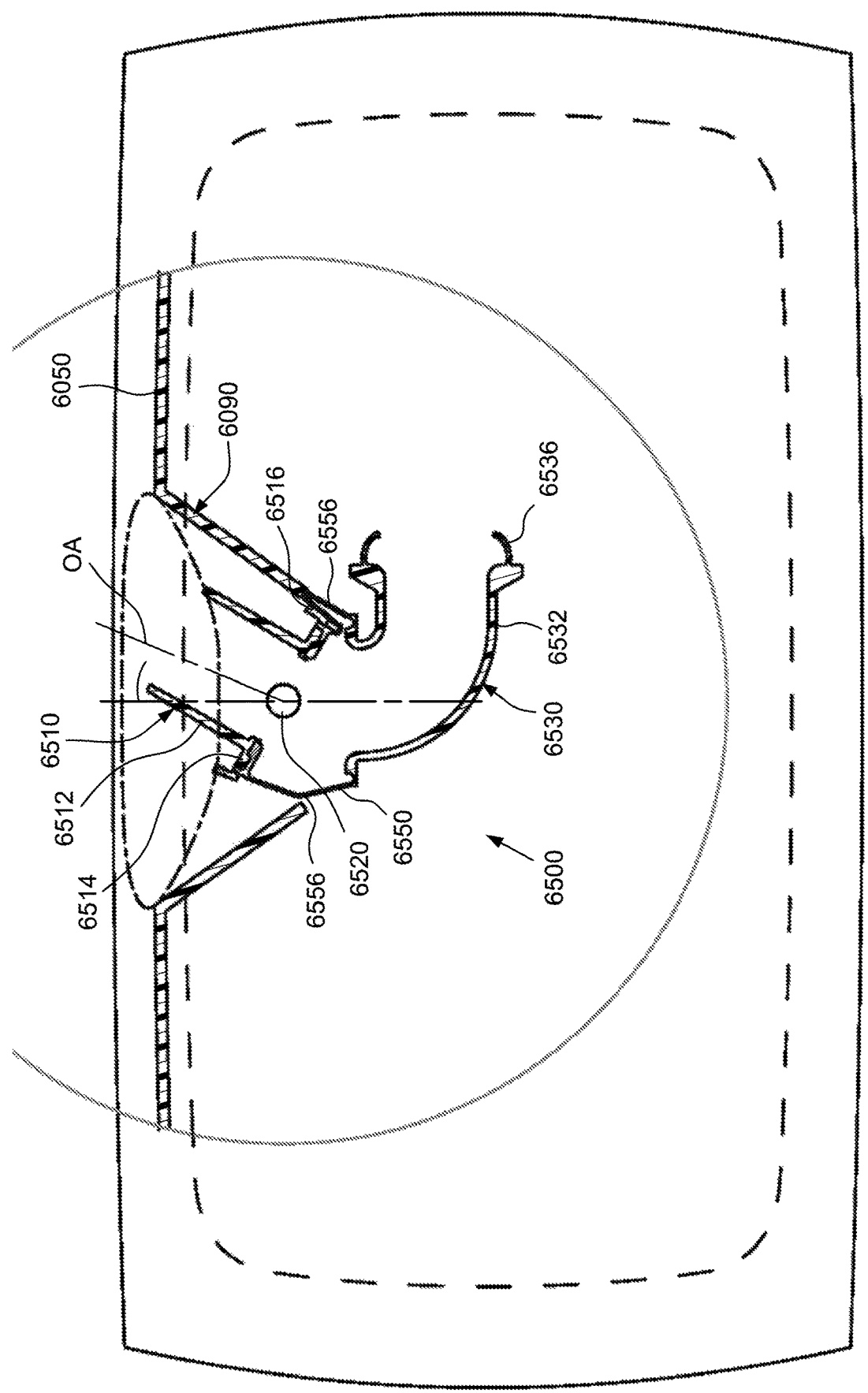
FIG. 14 is a cross-sectional view showing the pivotable outlet port of FIG. 5 with the outlet portion thereof pivoted to a maximum right position according to an example of the present technology.
Figure 15:
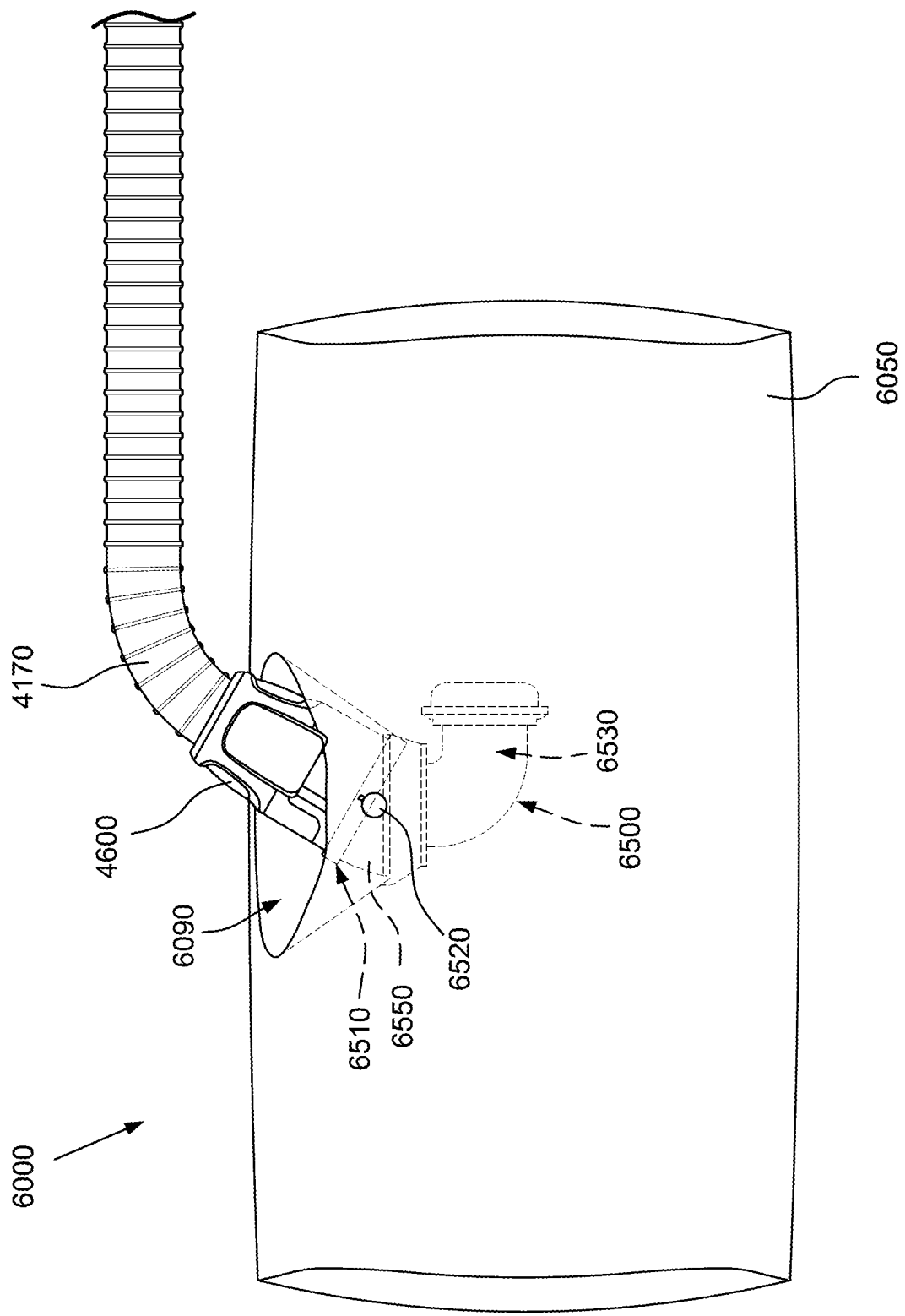
FIG. 15 is a top view showing air delivery tubing connected to the pivotable outlet port with the outlet portion thereof pivoted to the maximum right position of FIG. 14.
Figure 16:
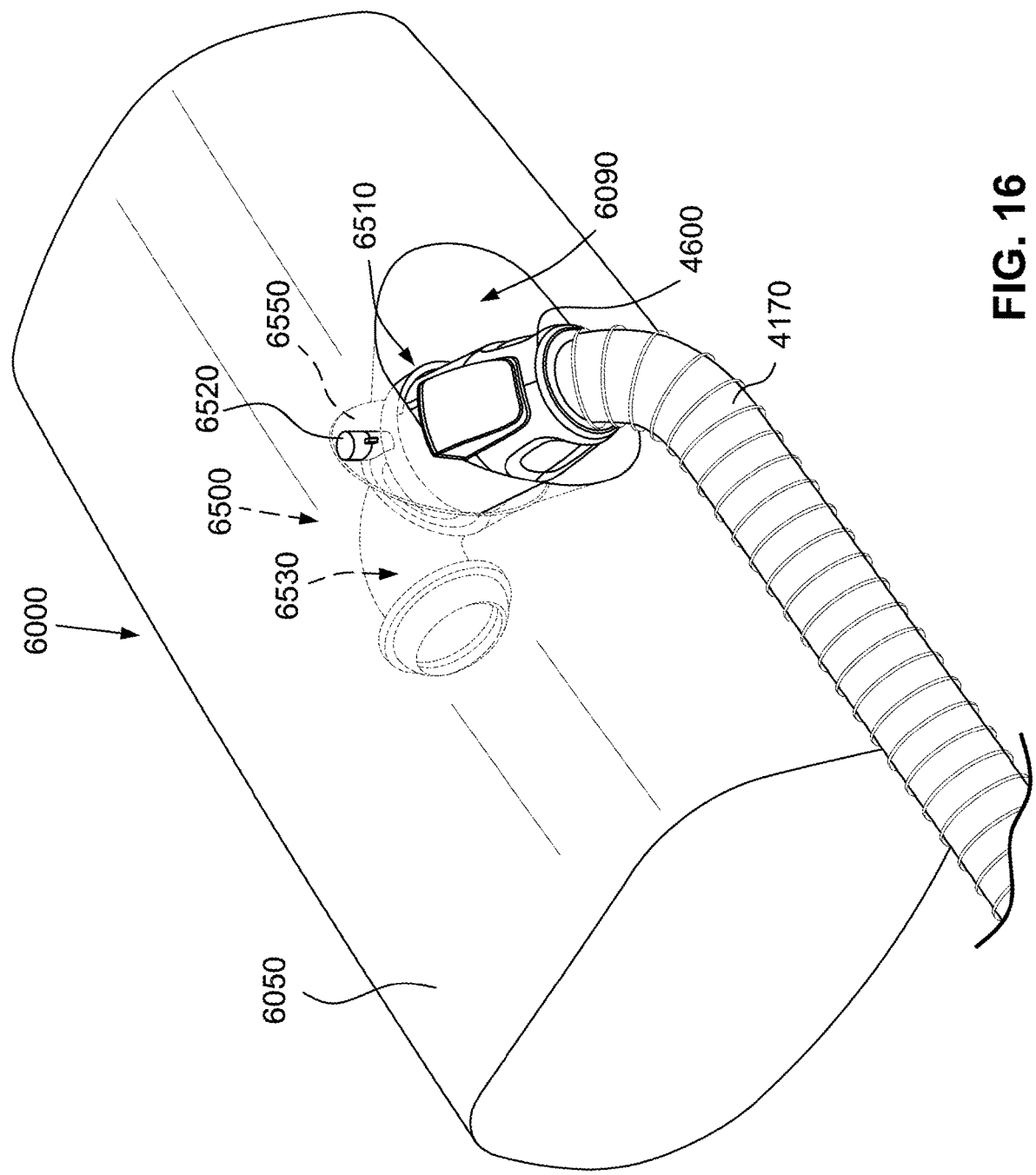
FIG. 16 is a perspective view showing air delivery tubing connected to the pivotable outlet port with the outlet portion thereof pivoted to the maximum right position of FIG. 14.

In an example, the end wall 6516 of the outlet portion 6510 may engage the gusset or fold 6556 of the decoupling portion 6550 which provides a stop to prevent further rotation when the outlet portion 6510 reaches the maximum left position and the maximum right position (as viewed in FIGS. 11 and 14).

As shown in FIGS. 11 and 14, when the decoupling portion 6550 is activated due to pivotal movement of the outlet portion 6510, the gusset or fold 6556 is structured and arranged expand and/or contract. For example, in the maximum left position (as viewed in FIG. 11), the left side of the gusset or fold 6556 contracts such that the flexible sides walls fold or flex towards one another while the right side of the gusset or fold 6556 expands such that the flexible sides walls fold or flex away from one another. Likewise, in the maximum right position (as viewed in FIG. 14), the right side of the gusset or fold 6556 contracts such that the flexible sides walls fold or flex towards one another while the left side of the gusset or fold 6556 expands such that the flexible sides walls fold or flex away from one another. When force applied to the air delivery tube 4170 is released, the outlet portion 6510 may resiliently return to its initial, rest position (e.g., as viewed in FIGS. 5 to 10) due to elasticity of the decoupling portion 6550.

In an example, the outlet portion 6510 may freely rotate to any position between the maximum left and right positions, e.g., depending on force applied to the air delivery tube 4170. In an alternative example, the pivotable outlet port 6500 may include a ratcheting or locking arrangement structured and arranged to provide one or more discrete and predetermined angular positions of the outlet portion 6510.

In a further alternative arrangement, not shown in the drawings, a ball joint type connection between the dock connector 4600 and the outlet port 6500 may also be used. Such an arrangement will allow decoupling of the outlet portion 6510 relative to the inlet portion 6530, and therefore decoupling of the air delivery tube 4170 from the RPT device in a plurality of planes, and not only in a single horizontal plane illustrated in FIGS. 5 to 16, allowing pivoting of the outlet portion 6510 and the air delivery tube with respect of a plurality of axes. Such a decoupling allows the conduit 4170 to be easily directed in many (not only horizontal) orientations, depending on the location of the patient, without exerting an unnecessary force on the stationary RPT device 4000.

5.6.2.4 Water Level Indicator

The humidifier reservoir 5110 may comprise a water level indicator. In some forms, the water level indicator may provide one or more indications to a user such as the patient 1000 or a care giver regarding a quantity of the volume of water in the humidifier reservoir 5110. The one or more indications provided by the water level indicator may include an indication of a maximum, predetermined volume of water, any portions thereof, such as 25%, 50% or 75% or volumes such as 200 ml, 300 ml or 400 ml.

5.6.2.5 Humidifier Transducer(s)

Figure 4:
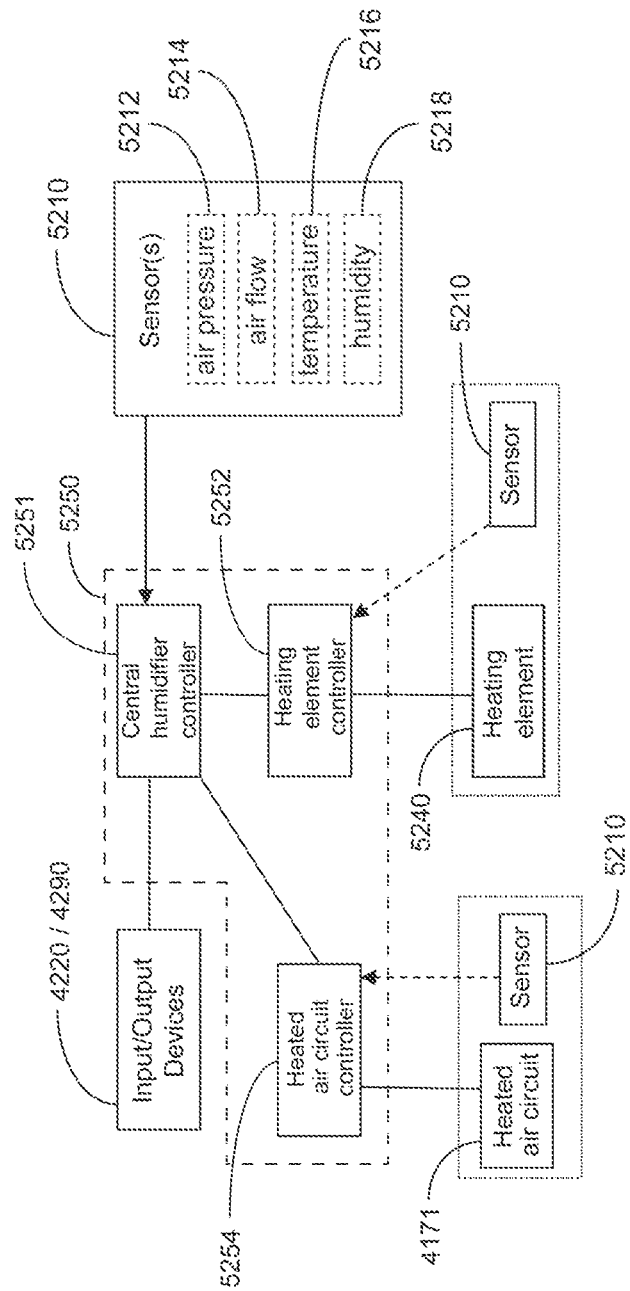
FIG. 4 shows a schematic of a humidifier in accordance with one form of the present technology.

As shown in FIG. 4, the humidifier 5000 may comprise one or more humidifier transducers (sensors) 5210 instead of, or in addition to, transducers provided in the RPT device 4000. Humidifier transducers 5210 may include one or more of an air pressure sensor 5212, an air flow rate transducer 5214, a temperature sensor 5216, or a humidity sensor 5218 as shown in FIG. 4. A humidifier transducer 5210 may produce one or more output signals which may be communicated to a controller such as the central controller of the RPT device 4000 and/or a humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor 4272 provided in the RPT device 4000.

5.6.2.5.2 Flow Rate Transducer

One or more flow rate transducers 5214 may be provided to the humidifier 5000 in addition to, or instead of, a flow rate sensor provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base where heat may be provided to the humidifier reservoir 5110 primarily by conduction.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal (1 hectopascal=100 Pa=100 N/m$^2$=1 millibar 0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9

REFERENCE SIGNS LIST

| Feature Item | Number |
| --- | --- |
| patient | 1000 |
| bed partner | 1100 |
| patient interface | 3000 |
| patient interface | 3000 |
| seal - forming structure | 3100 |
| plenum chamber | 3200 |
| positioning and stabilising structure | 3300 |
| vent | 3400 |
| connection port | 3600 |
| forehead support | 3700 |
| RPT device | 4000 |
| main panel | 4010 |
| front panel | 4012 |
| side panel | 4014 |

-continued

REFERENCE SIGNS LIST

| Feature Item | Number |
| --- | --- |
| chassis | 4016 |
| pneumatic block | 4020 |
| outlet muffler | 4124 |
| air circuit | 4170 |
| PCBA | 4202 |
| dock connector | 4600 |
| humidifier | 5000 |
| water reservoir | 5110 |
| heater plate | 5120 |
| water reservoir dock | 5130 |
| cavity | 5160 |
| dock air outlet | 5168 |
| dock air inlet | 5170 |
| humidifier outlet | 5172 |
| humidifier transducer | 5210 |
| air pressure sensor | 5212 |
| air flow rate transducer | 5214 |
| temperature sensor | 5216 |
| humidity sensor | 5218 |
| heating element | 5240 |
| humidifier controller | 5250 |
| central humidifier controller | 5251 |
| heating element controller | 5252 |
| air circuit controller | 5254 |
| integrated RPT device and humidifier | 6000 |
| reservoir dock | 6050 |
| dock outlet | 6090 |
| side wall | 6092 |
| opening | 6095 |
| pivotable outlet port | 6500 |
| outlet portion | 6510 |
| outlet tube | 6512 |
| flange | 6514 |
| end wall | 6516 |
| pivot pins | 6520 |
| inlet portion | 6530 |
| inlet tube | 6532 |
| flange | 6534 |
| inlet seal | 6536 |
| decoupling portion | 6550 |
| outlet end | 6552 |
| inlet end | 6554 |
| fold | 6556 |

The invention claimed is:

1. An apparatus for providing a pressurised flow of breathable gas to airways of a patient, the apparatus comprising:
a pivotable outlet port structured and arranged to connect to an air delivery tube configured to pass the pressurised flow of breathable gas to a patient interface, the pivotable outlet port being able to pivot about at least one axis,
wherein the pivotable outlet port includes an outlet portion pivotally coupled to the apparatus, an inlet portion adapted to receive the pressurised flow of breathable gas, and a decoupling portion that provides a decoupling connection between the inlet portion and the outlet portion,
wherein the outlet portion includes an outlet tube adapted to directly connect to the air delivery tube,
wherein the outlet portion comprises a direct pivotal connection to the apparatus configured to provide the pivotal coupling of the outlet portion to the apparatus about the at least one axis,
wherein the decoupling portion is structured and arranged to decouple pivotal movement of the outlet portion from the inlet portion, wherein the decoupling portion comprises a gusset or fold structured and arranged to expand and/or contract when the outlet portion is pivoted relative to the apparatus, and wherein the direct pivotal connection of the outlet portion is separate and distinct from the inlet portion and the decoupling portion.

2. The apparatus according to claim 1, wherein the decoupling portion is structured and arranged to allow the outlet portion to assume alternative positions or orientations relative to the apparatus for connection to the air delivery tube without impacting the inlet portion with respect to at least one plane associated with the apparatus.

3. The apparatus according to claim 1, wherein the outlet portion comprises a relatively rigid material and the inlet portion and the decoupling portion comprise a relatively soft and/or flexible material that is overmolded to the outlet portion.

4. The apparatus according to claim 3, wherein the outlet portion comprises a thermoplastic polymer.

5. The apparatus according to claim 3, wherein the inlet portion and the decoupling portion comprise a thermoplastic elastomer.

6. The apparatus according to claim 1, wherein the inlet portion includes an inlet seal.

7. The apparatus according to claim 1, wherein the outlet portion includes at least one pivot pin configured to provide the pivotal connection of the outlet portion.

8. The apparatus according to claim 1, wherein the outlet portion includes a pivotal range of movement, in at least one plane associated with the apparatus, which is within at least one of the following ranges; up to at least 30 degrees, up to at least 90 degrees, up to at least 180 degrees, and up to at least 270 degrees.

9. The apparatus according to claim 1, further comprising: a water reservoir including a cavity structured to hold a volume of water; and a water reservoir dock structured and arranged to receive the water reservoir in an operative position, wherein the pivotable outlet port is provided to a dock outlet of the water reservoir dock, the pivotable outlet port configured to pneumatically connect the water reservoir, or an outlet muffler, to the air delivery tube.

10. The apparatus according to claim 9, wherein the dock outlet includes a tapered side wall.

11. The apparatus according to claim 9, wherein the dock outlet is recessed with respect to an external wall of the apparatus.

12. The apparatus according to claim 11, wherein the dock outlet is located in a wall cavity so that no more than a portion of the outlet portion of the pivotal outlet port protrudes outside the wall cavity and beyond the external wall.

13. The apparatus according to claim 12, wherein no portion of the outlet portion of the pivotal outlet port protrudes outside the wall cavity.

14. The apparatus according to claim 1, wherein at least a portion of the outlet portion is configured to engage the decoupling portion to provide a stop to prevent further pivotal movement.

15. The apparatus according to claim 1, wherein the decoupling portion comprises an elastomeric material and is configured to resiliently return the outlet portion to an initial rest position when force applied to the air delivery tube is released.

16. An apparatus for providing a pressurised flow of breathable gas to airways of a patient, the apparatus comprising:

a pivotable outlet port structured and arranged to connect to an air delivery tube configured to pass the pressurised flow of breathable gas to a patient interface, the pivotable outlet port being able to pivot about at least one axis, wherein the pivotable outlet port includes an outlet portion pivotally coupled to the apparatus, an inlet portion adapted to receive the pressurised flow of breathable gas, and a decoupling portion that provides a decoupling connection between the inlet portion and the outlet portion, wherein the outlet portion includes at least one pivot pin configured to provide the pivotal coupling of the outlet portion to the apparatus about the at least one axis, wherein the outlet portion includes an outlet tube adapted to directly connect to the air delivery tube, and wherein the decoupling portion is structured and arranged to decouple pivotal movement of the outlet portion from the inlet portion.

17. The apparatus according to claim 16, wherein the at least one pivot pin is configured to allow the outlet portion to pivot relative to the apparatus about only a single axis.

18. The apparatus according to claim 16, wherein the apparatus forms a bottom plane that is substantially horizontal when the apparatus is in a working orientation, and the outlet portion is pivotally coupled to the apparatus such that the at least one axis is oriented generally perpendicular to the bottom plane.

19. The apparatus according claim 16, wherein the decoupling portion comprises a gusset or fold structured and arranged to expand and/or contract when the outlet portion is pivoted relative to the apparatus.

20. The apparatus according to claim 16, further comprising: a water reservoir including a cavity structured to hold a volume of water; and a water reservoir dock structured and arranged to receive the water reservoir in an operative position, wherein the pivotable outlet port is provided to a dock outlet of the water reservoir dock, the pivotable outlet port configured to pneumatically connect the water reservoir, or an outlet muffler, to the air delivery tube.

* * * * *